United States Patent
Salehian et al.

(10) Patent No.: US 11,350,853 B2
(45) Date of Patent: Jun. 7, 2022

(54) GAIT COACHING IN FITNESS TRACKING SYSTEMS

(71) Applicant: Under Armour, Inc., Baltimore, MD (US)

(72) Inventors: Hesamoddin Salehian, San Francisco, CA (US); Jeff Knight, Austin, TX (US); Marlene Mayfield, San Francisco, CA (US); Sebastian Johnck, San Francisco, CA (US)

(73) Assignee: Under Armour, Inc., Baltimore, MD (US)

( * ) Notice: Subject to any disclaimer, the term of this patent is extended or adjusted under 35 U.S.C. 154(b) by 594 days.

(21) Appl. No.: 16/150,095

(22) Filed: Oct. 2, 2018

(65) Prior Publication Data

US 2020/0100704 A1   Apr. 2, 2020

(51) Int. Cl.
*A61B 5/11* (2006.01)
*A61B 5/00* (2006.01)
(Continued)

(52) U.S. Cl.
CPC .......... *A61B 5/112* (2013.01); *A61B 5/6807* (2013.01); *A61B 5/742* (2013.01); *G16H 20/30* (2018.01);
(Continued)

(58) Field of Classification Search
CPC ....... A61B 5/112; A61B 5/742; A61B 5/1118; A61B 5/6807; A61B 2503/10; G16H 20/30; A63B 24/0075
See application file for complete search history.

(56) References Cited

U.S. PATENT DOCUMENTS

| 4,578,769 A | 3/1986 | Frederick |
| 5,636,146 A | 6/1997 | Flentov et al. |

(Continued)

FOREIGN PATENT DOCUMENTS

| WO | 2017/059368 A1 | 4/2014 |
| WO | 2015/057675 A1 | 4/2015 |

(Continued)

OTHER PUBLICATIONS

Mikos et al., Regression analysis of gait parameters and mobility measures in a healthy cohort for subject-specific normative values, Jun. 18, 2018, PLoS ONE 13(6): e0199215 (Year: 2018).*

*Primary Examiner* — Daniel R Miller
*Assistant Examiner* — Christian T Bryant
(74) *Attorney, Agent, or Firm* — Maginot, Moore & Beck, LLP

(57) ABSTRACT

A method of providing gait coaching is disclosed. Run data is received and stored regarding runs of a broad and diverse population of users, as well as a more narrow set of expert users. A gait metric model is developed for determining an ideal stride length or cadence based on pace and at least one physiological characteristic. Regression coefficients for at the model are determined based on a regression of the run data from the broad and diverse population of users. In contrast, a regression constant for the model is determined based on a regression of the run data from expert users. Using the model, an ideal stride length or cadence for a particular user on a particular run can be determined and utilized to provide useful monitoring, comparison, and feedback to the user regarding his or her stride length or cadence.

17 Claims, 19 Drawing Sheets

(51) Int. Cl.
*G16H 20/30* (2018.01)
*A63B 24/00* (2006.01)

(52) U.S. Cl.
CPC ......... *A61B 5/1118* (2013.01); *A61B 2503/10* (2013.01); *A63B 24/0075* (2013.01)

(56) References Cited

U.S. PATENT DOCUMENTS

| | | | |
|---|---|---|---|
| 5,851,193 A | 12/1998 | Arikka et al. | |
| 5,955,667 A | 9/1999 | Fyfe | |
| 5,960,380 A | 9/1999 | Flentov et al. | |
| 6,018,705 A | 1/2000 | Gaudet et al. | |
| 6,052,654 A | 4/2000 | Gaudet et al. | |
| 6,145,389 A | 11/2000 | Ebeling et al. | |
| 6,159,130 A | 12/2000 | Torvinen | |
| 6,266,623 B1 | 7/2001 | Vock et al. | |
| 6,298,314 B1 | 10/2001 | Blackadar et al. | |
| 6,301,964 B1 | 10/2001 | Fyfe et al. | |
| 6,493,652 B1 | 12/2002 | Ohlenbusch et al. | |
| 6,496,787 B1 | 12/2002 | Flentov et al. | |
| 6,498,994 B2 | 12/2002 | Vock et al. | |
| 6,499,000 B2 | 12/2002 | Flentov et al. | |
| 6,513,381 B2 | 2/2003 | Fyfe et al. | |
| 6,571,193 B1 | 5/2003 | Unuma et al. | |
| 6,611,789 B1 | 8/2003 | Darley | |
| 6,745,069 B2 | 6/2004 | Nissila et al. | |
| 6,856,934 B2 | 2/2005 | Vock et al. | |
| 6,876,947 B1 | 4/2005 | Darley et al. | |
| 6,898,550 B1 | 5/2005 | Blackadar et al. | |
| 6,941,239 B2 | 9/2005 | Unuma et al. | |
| 6,959,259 B2 | 10/2005 | Vock et al. | |
| 7,054,784 B2 | 5/2006 | Flentov et al. | |
| 7,057,551 B1 | 6/2006 | Vogt | |
| 7,062,225 B2 | 6/2006 | White | |
| 7,092,846 B2 | 8/2006 | Vock et al. | |
| 7,158,912 B2 | 1/2007 | Vock et al. | |
| 7,171,331 B2 | 1/2007 | Vock et al. | |
| 7,188,439 B2 | 3/2007 | DiBenedetto et al. | |
| 7,200,517 B2 | 4/2007 | Darley et al. | |
| 7,215,515 B2 | 5/2007 | Sugawara et al. | |
| 7,225,565 B2 | 6/2007 | DiBenedetto et al. | |
| 7,234,798 B2 | 6/2007 | Sanpei et al. | |
| 7,245,254 B1 | 7/2007 | Vogt | |
| 7,251,454 B2 | 7/2007 | White | |
| 7,353,137 B2 | 4/2008 | Vock et al. | |
| 7,428,471 B2 | 9/2008 | Darely et al. | |
| 7,428,472 B2 | 9/2008 | Darley et al. | |
| 7,451,056 B2 | 11/2008 | Flentov et al. | |
| 7,457,724 B2 | 11/2008 | Vock et al. | |
| 7,459,118 B2 | 12/2008 | Nasu et al. | |
| 7,467,060 B2 | 12/2008 | Kulach et al. | |
| 7,506,460 B2 | 3/2009 | DiBenedetto et al. | |
| 7,519,327 B2 | 4/2009 | White | |
| 7,617,071 B2 | 11/2009 | Darley et al. | |
| 7,620,520 B2 | 11/2009 | Vock et al. | |
| 7,623,987 B2 | 11/2009 | Vock et al. | |
| 7,627,451 B2 | 12/2009 | Vock et al. | |
| 7,631,382 B2 | 12/2009 | DiBenedetto et al. | |
| 7,670,263 B2 | 3/2010 | Ellis et al. | |
| 7,676,960 B2 | 3/2010 | DiBenedetto et al. | |
| 7,676,961 B2 | 3/2010 | DiBenedetto et al. | |
| 7,698,101 B2 | 4/2010 | Alten et al. | |
| 7,706,815 B2 | 4/2010 | Graham et al. | |
| 7,774,156 B2 | 8/2010 | Niva et al. | |
| 7,805,150 B2 | 9/2010 | Graham et al. | |
| 7,813,887 B2 | 10/2010 | Vock et al. | |
| 7,827,000 B2 | 11/2010 | Stirling et al. | |
| 7,856,339 B2 | 12/2010 | Vock et al. | |
| 7,901,326 B2 | 3/2011 | Niva et al. | |
| 7,905,815 B2 | 3/2011 | Ellis et al. | |
| 7,909,737 B2 | 3/2011 | Ellis et al. | |
| 7,931,562 B2 | 4/2011 | Ellis et al. | |
| 7,949,488 B2 | 5/2011 | Flentov et al. | |
| 7,953,549 B2 | 5/2011 | Graham et al. | |
| 7,962,312 B2 | 6/2011 | Darley et al. | |
| 7,983,876 B2 | 7/2011 | Vock et al. | |
| 8,021,312 B2 | 9/2011 | Kinnunen et al. | |
| 8,036,850 B2 | 10/2011 | Kulach et al. | |
| 8,036,851 B2 | 10/2011 | Vock et al. | |
| 8,055,469 B2 | 11/2011 | Kulach et al. | |
| 8,056,268 B2 | 11/2011 | DiBenedetto et al. | |
| 8,060,337 B2 | 11/2011 | Kulach et al. | |
| 8,070,654 B2 | 12/2011 | Chapa, Jr. et al. | |
| 8,083,646 B2 | 12/2011 | Chapa, Jr. et al. | |
| 8,092,345 B2 | 1/2012 | Ellis et al. | |
| 8,099,258 B2 | 1/2012 | Alten et al. | |
| 8,105,208 B2 | 1/2012 | Oleson et al. | |
| 8,126,675 B2 | 2/2012 | Vock et al. | |
| 8,128,410 B2 | 3/2012 | Prstojevich | |
| 8,154,554 B1 | 4/2012 | Brown et al. | |
| 8,251,875 B2 | 8/2012 | Ellis et al. | |
| 8,260,667 B2 | 9/2012 | Graham et al. | |
| 8,287,435 B2 | 10/2012 | Chapa, Jr. et al. | |
| 8,292,788 B2 | 10/2012 | Chapa, Jr. et al. | |
| 8,313,416 B2 | 11/2012 | Ellis et al. | |
| 8,337,212 B2 | 12/2012 | Prstojevich | |
| 8,352,211 B2 | 1/2013 | Vock et al. | |
| 8,360,936 B2 | 1/2013 | DiBenedetto et al. | |
| 8,428,904 B2 | 4/2013 | Vock et al. | |
| 8,452,259 B2 | 5/2013 | Ellis et al. | |
| 8,517,896 B2 | 8/2013 | Robinette et al. | |
| 8,538,691 B2 | 9/2013 | Haataja et al. | |
| 8,579,767 B2 | 11/2013 | Ellis et al. | |
| 8,602,946 B2 | 12/2013 | Chapa, Jr. et al. | |
| 8,620,585 B2 | 12/2013 | Graham et al. | |
| 8,645,059 B2 | 2/2014 | Tuulari | |
| 8,652,009 B2 | 2/2014 | Ellis et al. | |
| 8,652,010 B2 | 2/2014 | Ellis et al. | |
| 8,657,723 B2 | 2/2014 | Ellis et al. | |
| 8,660,814 B2 | 2/2014 | Vock et al. | |
| 8,694,136 B2 | 4/2014 | Ellis et al. | |
| 8,696,520 B2 | 4/2014 | Ellis et al. | |
| 8,702,430 B2 | 4/2014 | Dibenedetto et al. | |
| 8,712,725 B2 | 4/2014 | Darley et al. | |
| 8,721,342 B2 | 5/2014 | Prstojevich | |
| 8,721,502 B2 | 5/2014 | Ellis et al. | |
| 8,725,276 B2 | 5/2014 | Ellis et al. | |
| 8,740,751 B2 | 6/2014 | Shum | |
| 8,740,752 B2 | 6/2014 | Ellis et al. | |
| 8,762,092 B2 | 6/2014 | Vock et al. | |
| 8,775,120 B2 | 7/2014 | Molettiere et al. | |
| 8,795,137 B2 | 8/2014 | Ellis et al. | |
| 8,801,577 B2 | 8/2014 | Dibenedetto et al. | |
| 8,814,755 B2 | 8/2014 | Ellis et al. | |
| 8,827,869 B2 | 9/2014 | Ellis et al. | |
| 8,845,495 B2 | 9/2014 | Chapa, Jr. et al. | |
| 8,849,610 B2 | 9/2014 | Molettiere et al. | |
| 8,858,399 B2 | 10/2014 | Ellis et al. | |
| 8,880,377 B2 | 11/2014 | Niemimaki | |
| 8,894,548 B2 | 11/2014 | Ellis et al. | |
| 8,923,998 B2 | 12/2014 | Ellis et al. | |
| 8,944,959 B2 | 2/2015 | Chapa, Jr. et al. | |
| 8,965,732 B2 | 2/2015 | Robinette et al. | |
| 8,968,156 B2 | 3/2015 | Ellis et al. | |
| 9,028,430 B2 | 5/2015 | Woo et al. | |
| 9,028,432 B2 | 5/2015 | Woo et al. | |
| 9,044,149 B2 | 6/2015 | Richards et al. | |
| 9,044,171 B2 | 6/2015 | Venkatraman et al. | |
| 9,087,159 B2 | 7/2015 | Oleson et al. | |
| 9,126,070 B2 | 9/2015 | Prstojevich | |
| 9,137,309 B2 | 9/2015 | Ananny et al. | |
| 9,148,483 B1 | 9/2015 | Molettiere et al. | |
| 9,149,213 B2 | 10/2015 | Niemimaki | |
| 9,198,604 B2 | 12/2015 | Venkatraman et al. | |
| 9,223,936 B2 | 12/2015 | Aragones et al. | |
| 9,247,897 B2 | 2/2016 | Darley et al. | |
| 9,248,342 B2 | 2/2016 | Kampman | |
| 9,251,719 B2 | 2/2016 | Ellis et al. | |
| 9,267,793 B2 | 2/2016 | Vock et al. | |
| 9,282,902 B2 | 3/2016 | Richards et al. | |
| 9,283,430 B2 | 3/2016 | Woo et al. | |
| 9,302,170 B2 | 4/2016 | Balakrishnan et al. | |
| 9,314,685 B2 | 4/2016 | Balakrishuan et al. | |
| 9,352,207 B2 | 5/2016 | Balakrishnan et al. | |

(56) References Cited

U.S. PATENT DOCUMENTS

| | | | |
|---|---|---|---|
| 9,355,573 B2 | 5/2016 | Ellis et al. |
| 9,369,365 B2 | 6/2016 | Molettier et al. |
| 9,382,220 B2 | 7/2016 | Crankson et al. |
| 9,392,941 B2 | 7/2016 | Powch et al. |
| 9,401,098 B2 | 7/2016 | Ellis |
| 9,402,552 B2 | 8/2016 | Richards et al. |
| 9,415,267 B2 | 8/2016 | Ellis |
| 9,424,397 B2 | 8/2016 | Werner et al. |
| 9,446,287 B2 | 9/2016 | Weast et al. |
| 9,453,742 B2 | 9/2016 | Capozzi et al. |
| 9,456,781 B2 | 10/2016 | Balakrishnan et al. |
| 9,459,118 B2 | 10/2016 | Pham |
| 9,468,808 B2 | 10/2016 | Balakrishnan et al. |
| 9,478,148 B2 | 10/2016 | Ellis |
| 9,478,149 B2 | 10/2016 | Ellis |
| 9,489,863 B2 | 11/2016 | Ellis |
| 9,523,704 B2 | 12/2016 | Blakrishnan et al. |
| 9,526,430 B2 | 12/2016 | Srinivas et al. |
| 9,529,011 B2 | 12/2016 | Balakrishnan et al. |
| 9,546,871 B2 | 1/2017 | Ellis et al. |
| 9,572,533 B2 | 2/2017 | Vankatraman et al. |
| 9,589,480 B2 | 3/2017 | Ellis |
| 9,597,014 B2 | 3/2017 | Venkatraman et al. |
| 9,623,316 B2 | 4/2017 | Chapa, Jr. et al. |
| 9,625,485 B2 | 4/2017 | Oleson et al. |
| 9,645,165 B2 | 5/2017 | Oleson et al. |
| 9,662,053 B2 | 5/2017 | Richards et al. |
| 9,675,281 B2 | 6/2017 | Arnold et al. |
| 9,679,494 B2 | 6/2017 | Ellis |
| 9,683,847 B2 | 6/2017 | Ellis |
| 9,694,241 B2 | 7/2017 | Balakrishnan et al. |
| 9,700,760 B2 | 7/2017 | Poyhtari et al. |
| 9,702,899 B2 | 7/2017 | Miller et al. |
| 9,711,062 B2 | 7/2017 | Ellis et al. |
| 9,712,629 B2 | 7/2017 | Molettiere et al. |
| 9,730,027 B2 | 8/2017 | Su et al. |
| 9,759,738 B2 | 9/2017 | Oleson et al. |
| 9,767,709 B2 | 9/2017 | Ellis |
| 9,808,185 B2 | 11/2017 | Arnold et al. |
| 9,810,709 B2 | 11/2017 | Blakrishnan et al. |
| 9,814,937 B2 | 11/2017 | Werner et al. |
| 2005/0195094 A1 | 9/2005 | White |
| 2007/0006489 A1 | 1/2007 | Case, Jr. et al. |
| 2007/0275826 A1 | 11/2007 | Miemimaki et al. |
| 2008/0058971 A1 | 3/2008 | Graham et al. |
| 2009/0174558 A1 | 7/2009 | White |
| 2010/0188405 A1 | 7/2010 | Haughay, Jr. et al. |
| 2012/0010478 A1 | 1/2012 | Kinnunen et al. |
| 2012/0015778 A1 | 1/2012 | Lee et al. |
| 2012/0173978 A1 | 7/2012 | Lee et al. |
| 2013/0085677 A1 | 4/2013 | Modi et al. |
| 2013/0085700 A1 | 4/2013 | Modi et al. |
| 2013/0085711 A1 | 4/2013 | Modi et al. |
| 2013/0151193 A1 | 6/2013 | Kulach et al. |
| 2013/0178958 A1 | 7/2013 | Kulach et al. |
| 2013/0184613 A1 | 7/2013 | Homsi et al. |
| 2013/0185016 A1 | 7/2013 | Homsi et al. |
| 2014/0074431 A1 | 3/2014 | Modi |
| 2014/0088869 A1 | 3/2014 | Graham et al. |
| 2014/0129239 A1 | 5/2014 | Utter, II |
| 2014/0156215 A1* | 6/2014 | Eastman ............ A61B 5/112 702/141 |
| 2014/0171266 A1 | 6/2014 | Hawkins, III et al. |
| 2014/0171272 A1 | 6/2014 | Hawkins, III et al. |
| 2014/0173443 A1 | 6/2014 | Hawkins, III et al. |
| 2014/0200847 A1 | 7/2014 | Singiresu et al. |
| 2014/0266780 A1 | 9/2014 | Rahman et al. |
| 2014/0278208 A1 | 9/2014 | Donaldson |
| 2014/0288875 A1 | 9/2014 | Donaldson |
| 2014/0288876 A1 | 9/2014 | Donaldson |
| 2014/0288877 A1 | 9/2014 | Donaldson |
| 2014/0288878 A1 | 9/2014 | Donaldson |
| 2014/0303900 A1 | 10/2014 | Rahman et al. |
| 2014/0306821 A1 | 10/2014 | Rahman et al. |
| 2014/0342329 A1 | 11/2014 | Debenedetto et al. |
| 2014/0379107 A1 | 12/2014 | Arjomand |
| 2015/0099945 A1* | 4/2015 | Hawkins, III ........ G01C 22/002 600/301 |
| 2015/0106052 A1 | 4/2015 | Balakrishnan et al. |
| 2015/0141202 A1 | 5/2015 | Ellis et al. |
| 2015/0153330 A1 | 6/2015 | Tan et al. |
| 2015/0153374 A1 | 6/2015 | Balakrishnan et al. |
| 2015/0185045 A1 | 7/2015 | Crawford et al. |
| 2015/0243187 A1 | 8/2015 | Graham et al. |
| 2015/0269866 A1 | 9/2015 | Ellis et al. |
| 2015/0285659 A1 | 10/2015 | Curtis et al. |
| 2015/0286673 A1 | 10/2015 | Graham et al. |
| 2015/0335291 A1 | 11/2015 | Saadi et al. |
| 2015/0350840 A1 | 12/2015 | Pham et al. |
| 2015/0375043 A1 | 12/2015 | Prstojevich |
| 2016/0022175 A1 | 1/2016 | Arnold et al. |
| 2016/0022203 A1 | 1/2016 | Arnold et al. |
| 2016/0034634 A9 | 2/2016 | Hong et al. |
| 2016/0045159 A1 | 2/2016 | Balakrishnan et al. |
| 2016/0054449 A1 | 2/2016 | Pekonen et al. |
| 2016/0058302 A1 | 3/2016 | Raghuram et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0114213 A1* | 4/2016 | Lee .................. A63B 24/0075 434/255 |
| 2016/0120414 A1 | 5/2016 | Darley et al. |
| 2016/0133142 A1 | 5/2016 | Ellis |
| 2016/0140867 A1 | 5/2016 | Aragones et al. |
| 2016/0195566 A1 | 7/2016 | Vock et al. |
| 2016/0196325 A1 | 7/2016 | Andon et al. |
| 2016/0213974 A1 | 7/2016 | Balakrishnan et al. |
| 2016/0223580 A1 | 8/2016 | Balakrishnan et al. |
| 2016/0235363 A9 | 8/2016 | Karavirts |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0273918 A1 | 9/2016 | Graham et al. |
| 2016/0275814 A1 | 9/2016 | Ellis et al. |
| 2016/0334433 A1 | 11/2016 | Kazemi |
| 2016/0345891 A1 | 12/2016 | Kirby et al. |
| 2016/0346604 A1 | 12/2016 | Lindstrom et al. |
| 2016/0346614 A1 | 12/2016 | Kirby et al. |
| 2016/0349077 A1 | 12/2016 | Capozzi et al. |
| 2016/0354635 A1 | 12/2016 | Weast et al. |
| 2016/0356804 A1 | 12/2016 | Miller et al. |
| 2016/0367191 A1* | 12/2016 | Esposito ................ D04B 1/14 |
| 2016/0367855 A1 | 12/2016 | Balakrishnan et al. |
| 2016/0379518 A1 | 12/2016 | Balakrishnan et al. |
| 2017/0031650 A1 | 2/2017 | Fraga et al. |
| 2017/0059327 A1 | 3/2017 | Miller |
| 2017/0059602 A1 | 3/2017 | Miller |
| 2017/0095181 A1 | 4/2017 | Hauenstein et al. |
| 2017/0095692 A1 | 4/2017 | Chang et al. |
| 2017/0095693 A1 | 4/2017 | Chang et al. |
| 2017/0120109 A1 | 5/2017 | Balakrishnan et al. |
| 2017/0127978 A1 | 5/2017 | Suydam et al. |
| 2017/0148282 A1 | 5/2017 | Granlund et al. |
| 2017/0157466 A1 | 6/2017 | Korpela et al. |
| 2017/0160398 A1 | 6/2017 | Venkatraman et al. |
| 2017/0173393 A1 | 6/2017 | Chapa, Jr. et al. |
| 2017/0182360 A1 | 6/2017 | Chang et al. |
| 2017/0188893 A1 | 7/2017 | Vankatraman et al. |
| 2017/0188894 A1 | 7/2017 | Chang et al. |
| 2017/0189752 A1 | 7/2017 | Mohrman et al. |
| 2017/0212666 A1 | 7/2017 | Hawkins, III et al. |
| 2017/0213382 A1 | 7/2017 | Torvinen et al. |
| 2017/0224255 A1 | 8/2017 | Balakrishnan et al. |
| 2017/0227375 A1 | 8/2017 | Parikh et al. |
| 2017/0258374 A1 | 9/2017 | Ly et al. |
| 2017/0266493 A1 | 9/2017 | Balakrishnan et al. |
| 2017/0273601 A1 | 9/2017 | Wang et al. |
| 2017/0303827 A1 | 10/2017 | Giedwoyn et al. |

(56) References Cited

U.S. PATENT DOCUMENTS

2017/0340920 A1 11/2017 Posio et al.
2017/0344919 A1 11/2017 Chang et al.

FOREIGN PATENT DOCUMENTS

| | | |
|---|---|---|
| WO | 2015/057679 A1 | 4/2015 |
| WO | 2015/057701 A1 | 4/2015 |
| WO | 2015/060894 A1 | 4/2015 |
| WO | 2015/061805 A1 | 4/2015 |
| WO | 2015/061806 A1 | 4/2015 |
| WO | 2015/065925 A1 | 5/2015 |
| WO | 2015/079096 A1 | 6/2015 |
| WO | 2015/084793 A1 | 6/2015 |
| WO | 2015/084839 A1 | 6/2015 |
| WO | 2015/152921 A1 | 10/2015 |
| WO | 2016/029233 A1 | 2/2016 |
| WO | 2015/057684 A1 | 4/2016 |
| WO | 2016/112021 A1 | 7/2016 |
| WO | 2016/191461 A1 | 12/2016 |
| WO | 2016/195767 A1 | 12/2016 |
| WO | 2016/196254 A1 | 12/2016 |
| WO | 2016/196265 A1 | 12/2016 |
| WO | 2016/196272 A1 | 12/2016 |
| WO | 2016/196289 A1 | 12/2016 |
| WO | 2016/196295 A1 | 12/2016 |
| WO | 2016/196333 A1 | 12/2016 |
| WO | 2017/023717 A1 | 2/2017 |
| WO | 2017/083502 A1 | 5/2017 |
| WO | 2017/156267 A1 | 9/2017 |
| WO | 2017/201298 A1 | 11/2017 |
| WO | 2017/213962 A1 | 12/2017 |

\* cited by examiner

200

- 210 — Receive first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length.

- 220 — Determine regression coefficients for at least one gait metric model by performing a regression of the first historical run data, the at least one gait metric model being configured to output the gait metric given inputs of pace and the at least one physiological characteristic.

- 230 — Receive second historical run data regarding runs of a second plurality of users, the second historical run data including, for each run, the gait metric for the respective run, a pace during the respective run, and the at least one physiological characteristic of the respective user.

- 240 — Determine a regression constant for the at least one gait metric model by performing a regression of the second historical run data.

*FIG. 6*

GAIT COACHING IN FITNESS TRACKING SYSTEMS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The device and method disclosed in fitness tracking systems and, more particularly, to gait coaching in fitness tracking systems.

BACKGROUND

Activity tracking devices are increasingly utilized by individuals interested in tracking metrics related to their personal health and fitness activity. These activity tracking devices include, for example, heart rate monitors, step counters, stair counters, global positioning system ("GPS") tracking devices, as well as various other motion and biometric tracking devices. One of the most popular fitness activities for weight loss and general health is running. However, a common problem for maintaining a long term running habit is the risk of injury. It is well established that proper running gait (also referred to herein as running form) is one the best ways for runners to minimize the risk of injury. Additionally, proper running gait also improves running economy or, in other words, the amount of effort required to run at a given pace. Unfortunately, typical guidelines for proper running gait fall short of providing beginner and intermediate runners with the necessary tools to achieve and maintain a proper running gait. Particularly, typical guidelines are one-size-fits-all standards that fail to consider the unique physiological characteristics of the runner. Furthermore, even with appropriate guidelines, it is challenging for users to know how their running gait differs from the recommended gait. Accordingly, for many runners, the typical guidelines may be difficult to apply and sometimes counterproductive. In view of the foregoing, it would be advantageous to provide a method of gait coaching that was unique to the individual runner. It would also be advantageous if the method provided the user with specific guidance for how to change his or her gait to achieve and maintain the proper running gait.

SUMMARY

In accordance with one exemplary embodiment of the disclosures, a method of displaying run data is disclosed. The method comprises: receiving first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length; determining regression coefficients for at least one gait metric model by performing a regression of the first historical run data, the at least one gait metric model being configured to output the gait metric given inputs of pace and the at least one physiological characteristic; receiving second historical run data regarding runs of a second plurality of users, the second historical run data including, for each run, the gait metric for the respective run, a pace during the respective run, and the at least one physiological characteristic of the respective user; determining a regression constant for the at least one gait metric model by performing a regression of the second historical run data; receiving first run data from an activity monitoring device carried by a first user during a first run of the first user; determining the gait metric for the first run based on the first run data; determining a pace during the first run based on the first run data; determining a gait metric target for the first run based on the at least one gait metric model, the determined regression coefficients, the determined regression constant, the pace during the first run, and the at least one physiological characteristic of the first user; and displaying a comparison of the gait metric with the gait metric target to the first user on a personal electronic device associated with the first user.

Pursuant to another exemplary embodiment of the disclosures, a fitness tracking system is disclosed. The fitness tracking system comprises a database configured to store: first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length; and second historical run data regarding runs of a second plurality of users, the second historical run data including, for each run, the gait metric for the respective run, a pace during the respective run, and the at least one physiological characteristic of the respective user. The fitness tracking system comprises a data processor in communication with the database, the data processor being configured to: receive the first historical run data and the second historical run data from the database; determine regression coefficients for at least one gait metric model by performing a regression of the first historical run data, the at least one gait metric model being configured to output the gait metric given inputs of pace and the at least one physiological characteristic; determine a regression constant for the at least one gait metric model by performing a regression of the second historical run data; and transmit the regression coefficients and the regression constant for the at least one gait metric model to at least one personal electronic device of at least one user.

In accordance with yet another exemplary embodiment, a further method of displaying run data is disclosed. The method comprises: receiving first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length; determining regression coefficients for at least one gait metric model by performing a regression of the first historical run data, the at least one gait metric model being configured to output the gait metric given inputs of pace and the at least one physiological characteristic; receiving second historical run data regarding runs of a second plurality of users, the second historical run data including, for each run, the gait metric for the respective run, a pace during the respective run, and the at least one physiological characteristic of the respective user; determining a regression constant for the at least one gait metric model by performing a regression of the second historical run data; receiving first real-time run data from an activity monitoring device carried by a first user during a first run of the first user; determining a real-time value of the gait metric during the first run based on the first real-time run data; determining a real-time pace during the first run based on the first real-time run data; determining a real-time gait metric target during the first run based on the at least one gait metric model, the determined regression coefficients, the determined regression constant, the real-time pace during the first run, and the at least one physiological characteristic of the first user; and providing perceptible feedback to the first user during the first run depending on a comparison of the real-time value of the gait metric with the real-time gait metric target to the first user using a personal electronic device associated with the first user.

These and other aspects of the disclosure shall become apparent when considered in light of the disclosure provided herein.

BRIEF DESCRIPTION OF THE DRAWINGS

The foregoing aspects and other features of a fitness tracking system are explained in the following description, taken in connection with the accompanying drawings.

FIG. 6 is a logical flow diagram of a method of generating a gait metric model for determining an ideal running gait for a user.

All Figures © Under Armour, Inc. 2018. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Fitness Tracking System

Figure 1:
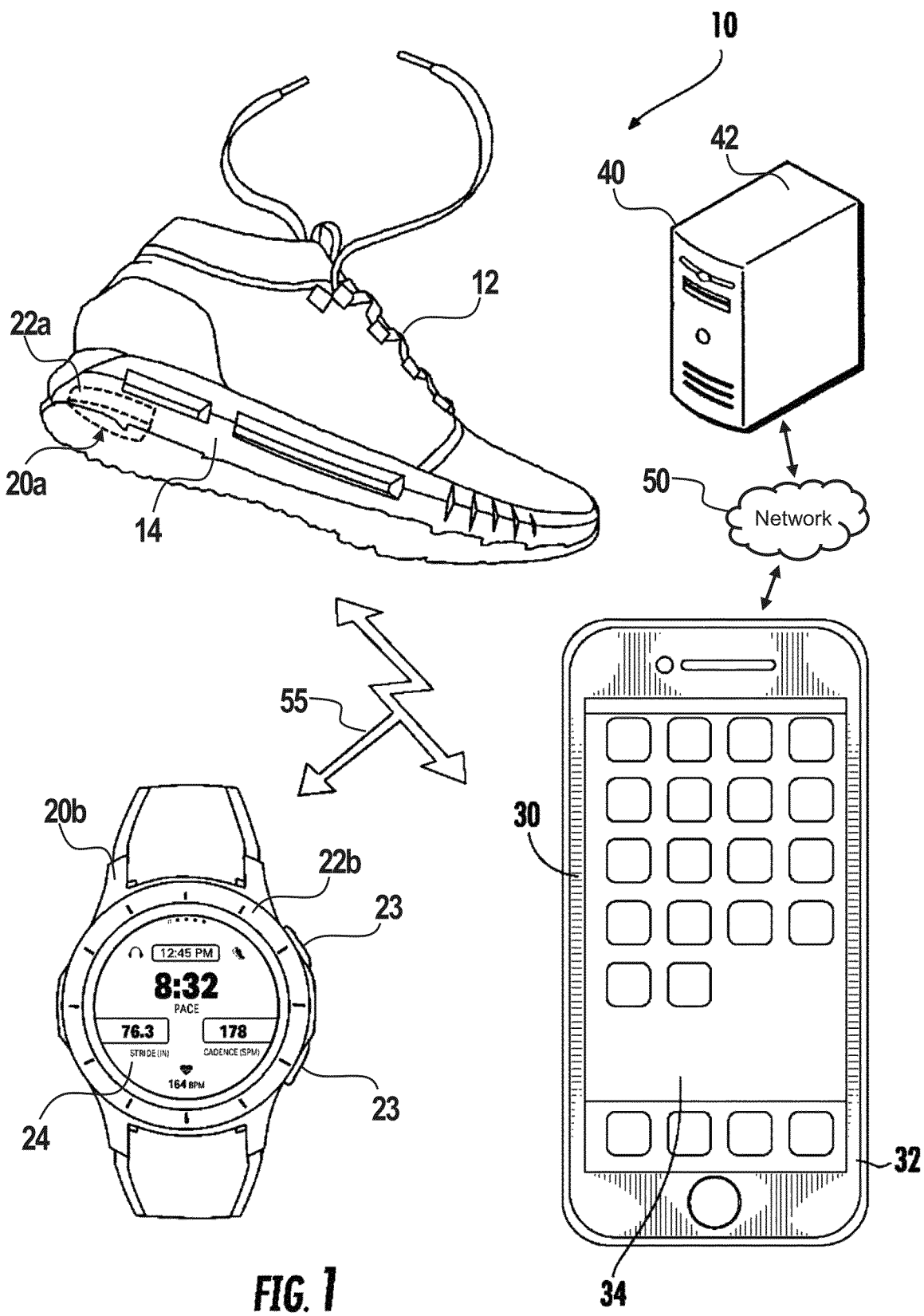
FIG. 1 is a diagrammatic view showing an exemplary embodiment of a fitness tracking system including activity monitoring devices, an electronic display device, and a system server.
Figure 2:
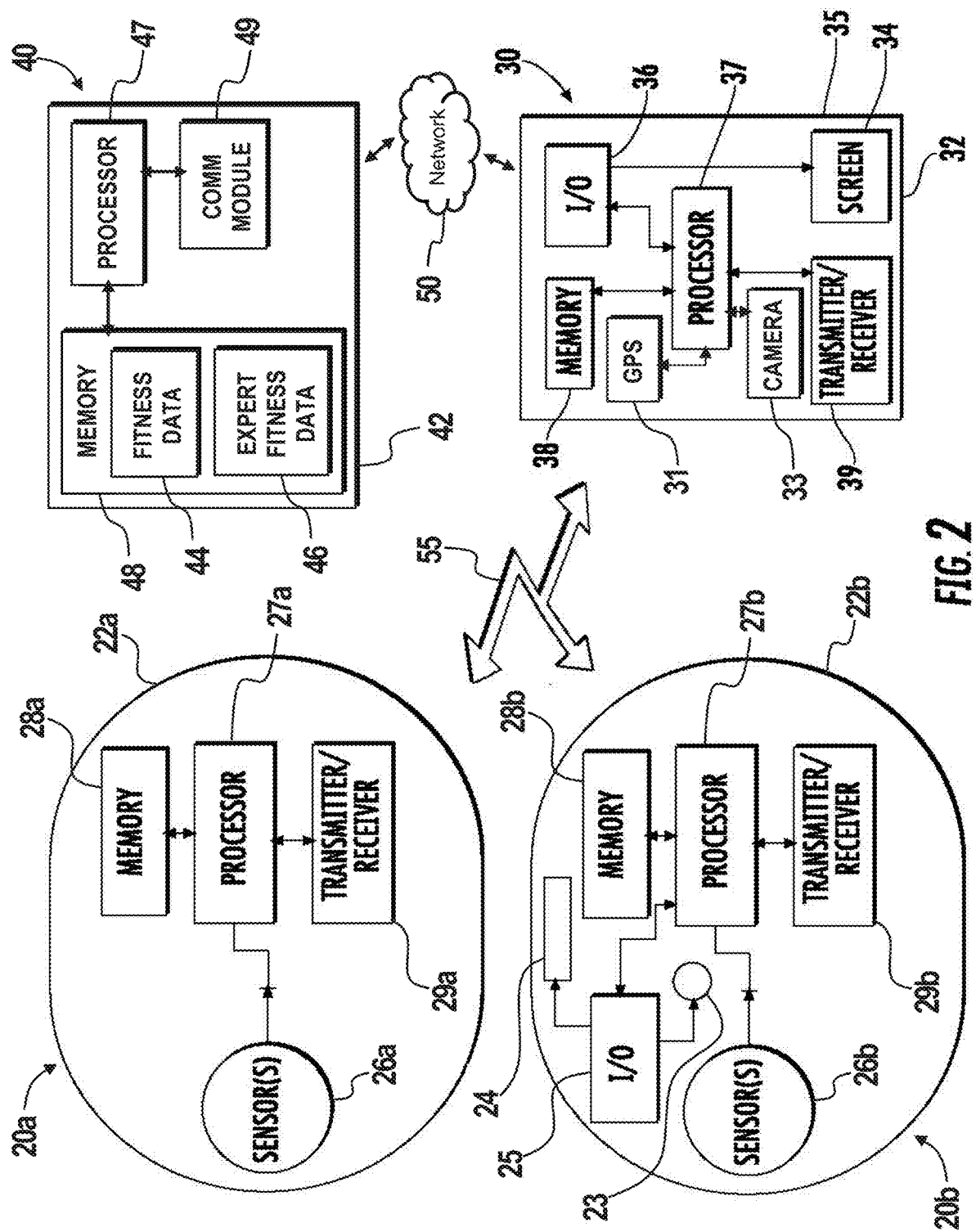
FIG. 2 is a block diagram of exemplary electronic components in the activity monitoring devices, the electronic display device, and the system server of the fitness tracking system of FIG. 1.

With reference to FIGS. 1-2, an exemplary embodiment of a fitness tracking system 10 for recording fitness data during an activity or workout (which may also be referred to herein as the "health tracking system" or the "activity tracking system"). The fitness tracking system 10 includes at least one activity monitoring device 20a, 20b and at least one electronic display device 30 in communication therewith. In at least one embodiment, the fitness tracking system 10 further includes a remote system server 40 in communication with at least the electronic display device 30 via a network 50, such as the Internet. The activity monitoring device(s) 20a, 20b are user devices configured to measure one or more health and fitness parameters of a user during an activity or workout and provide fitness data regarding the activity or workout to the electronic display device 30. In many embodiments, the activity monitoring device(s) 20a, 20b are designed and dimensioned to be worn on or carried by the body of a user. In the illustrated embodiment, the activity monitoring device 20a is integrated within a running shoe 12 and the activity monitoring device 20b is in the form of a so-called "smart" watch which is worn on the user's wrist. However, the activity monitoring devices may also be a designed and dimensioned to be worn by the user, for example, on his or her waist or ankle. In some embodiments, the fitness tracking system 10 includes further activity monitoring device(s) associated with the individual user. The electronic display device 30 is in the form of a smartphone and is designed to process the fitness data and display it to the user in a format that summarizes a user's performance during an activity or workout. In some embodiments, the electronic display device 30 may also collect fitness data independently of any dedicated activity monitoring device(s) and, in this way, may function as the activity monitoring device or as one of the activity monitoring devices.

The term "fitness data" as used herein refers to data relating to a user's fitness and performance during an activity or workout, but also data regarding the user's health and general well-being outside of the activity or workout, and may also be referred to herein as "fitness information" or "fitness parameters." Fitness data may include activity data and physiological data. Fitness data may be in a raw measured form or in a processed form. Fitness data may be automatically measured, sensed, or collected by the activity monitoring devices 20a, 20b and/or the electronic display device 30, but may also be entered manually by the user via the activity monitoring devices 20a, 20b and/or the electronic display device 30. The term "activity data" as used herein is a subset of fitness data, and refers to data related to physical activity (i.e., movement or lack thereof) of the user. Examples of activity data include body motion/acceleration data, step data, stride length data, stride cadence data, foot strike data, distance traversal data, pace/speed data, altitude data, environmental/positional data (such that provided by a GPS receiver), exercise weight/resistance data, exercise repetition data, and/or any of various other types of personal activity metrics that may be relevant to the user's physical activity for a given period of time. The term "physiological data" as used herein is a subset of fitness data, and refers to data related to the physiological status and health of the user. Examples of physiological data include age, gender, height, body weight, body fat, heart rate, aspiration rate, blood oxygenation, blood glucose, hydration, caloric expenditure, or any of various other types of physiological metrics that may be relevant the user's physiological health for a given period of time.

While the activity monitoring device(s) 20a, 20b are described herein as the primary devices for collecting and transmitting fitness data to the electronic display device 30, it will be recognized that additional data may also be collected or otherwise obtained and/or input in to the electronic display device 30 via various other mechanisms. In at least one embodiment, the user may manually input data directly into the activity monitoring device 20b and/or the electronic display device 30. For example, the user may manually collect exercise weight/resistance data or exercise repetition data and input such data into the activity monitoring device 20b and/or the electronic display device 30 without the use of a sensor and/or other device for transmitting the fitness data to the electronic display device 30.

Fitness data from the activity monitoring device(s) 20a, 20b are delivered to the electronic display device 30. As represented by the arrow 55 in FIGS. 1 and 2, the activity monitoring device(s) 20a, 20b are configured to transmit a wireless RF signal representative of the fitness data collected or obtained thereat to the electronic display device 30. In addition, the fitness data may also be transmitted to additional computing devices, such as a personal computer and/or a laptop computer where the fitness data may be conveniently displayed for the user. In other embodiments, a wired connection may be utilized for communication of fitness data between the electronic display device 30 and the activity monitoring device(s) 20a, 20b. Similarly, in another embodiment, the fitness data may be transmitted from the activity monitoring device(s) 20a, 20b and/or the electronic display device 30 to the system server 40. The data may then be accessed by the user at any number of additional computerized devices via a username and password, or other form of identification and authentication of the user.

The remote system server 40 comprises a computerized device or data processing system configured to run one or more software applications on a processor thereof for storing and processing fitness data. The activity monitoring device(s) 20a, 20b and electronic display device 30 may communicate via the network 55 to the system server 40 for storage and/or processing of the fitness data, thereby decreasing the processing capacity required at either user device (e.g., the activity monitoring device(s) 20a, 20b or electronic display device 30). In at least one embodiment, the remote system server 40 maintains a database of fitness data received from the electronic display device 30 and/or the activity monitoring device(s) 20a, 20b, as well as fitness data received from further electronic display devices and/or activity monitoring devices associated with a plurality of other users.

In at least one embodiment, the transmission of data from the activity monitoring device(s) 20a, 20b to the electronic display device 30 or to the system server 40 occurs automatically without requiring the user to prompt or initiate the transmission. In another embodiment, the activity monitoring device(s) 20a, 20b may be configured to begin transmissions once it receives a confirmation that the electronic display device 30 is within an appropriate range of the activity monitoring device(s) 20a, 20b. In yet another embodiment, data transmission may occur periodically at predetermined intervals of time. In other embodiments, where communications between the activity monitoring device(s) 20*a*, 20*b* and the electronic display device 30 are made with a wired connection, communications only occur when the wired connection is established between the activity monitoring device(s) 20*a*, 20*b* and the electronic display device 30. Similar logic applies to the transmission of data from the activity monitoring device(s) 20*a*, 20*b* and/or the electronic display device 30 to the system server 40.

Activity Monitoring Devices

With continued reference to FIGS. 1-2, the activity monitoring device(s) 20*a*, 20*b* (which may also be referred to herein as "activity tracking devices", or a "sensor devices") may be provided in any of various forms and is configured to measure, collect and/or otherwise obtain any of the various types of fitness data (as discussed above). The fitness data accumulated during an activity or workout may be collected automatically by a sensor of the activity monitoring device(s) 20*a*, 20*b*, via manual entry by the user, and/or collected by any of various other means. At least the activity monitoring device 20*a*, which is integrated with the running shoe 12, is configured to measure fitness data relating to user's running or walking, in particular the user's gait or form while running or walking. Particularly, the activity monitoring device 20*a* is configured to measure one or more of steps, distance, speed, stride length, stride cadence, pronation/supination angles, ground contact time, foot strike forces/directions, stairs climbed, as well as various other types of activity data or physiological data. The activity monitoring device 20*b* may be configured to measure additional fitness data and/or work in conjunction with the activity monitoring device 20*a* to measure the aforementioned data.

As discussed above, in the embodiment shown in FIG. 1, the activity monitoring device 20*a* is provided as a sensor device that is integrated within the running shoe 12. In at least one embodiment, the activity monitoring device 20*a* is non-removably embedded in a mid-sole 14 of the running shoe 12. However, in other embodiments, the activity monitoring device 20*a* may removably inserted into a portion of the shoe 12 or clipped or otherwise attached to an external surface of the shoe 12. As used herein, the term "shoe" refers to any type of footwear, such as tennis shoes, running shoes, casual shoes, boots, cleats, sandals, socks, or any other apparel, garment, clothing, or the like worn on a foot. In one embodiment, the activity monitoring device 20*a* includes a protective outer shell or housing 22*a* designed to retain and protect various sensors and other electronic components positioned within the housing 22*a*. The housing 22*a* comprise any number of shapes, configurations, and/or materials, the description herein being merely exemplary. In at least one embodiment, the housing 22*a* comprises a relatively rigid shell that securely retains the electronic components housed therein.

In the embodiment shown in FIG. 1, the activity monitoring device 20*b* is provided as a "smart" watch that the user straps to his or her wrist. The activity monitoring device 20*b* includes a protective outer shell or housing 22*b* designed to retain and protect various sensors and other electronic components positioned within the housing 22*b*. The housing 22*b* comprise any number of shapes, configurations, and/or materials, the description herein being merely exemplary. In one embodiment, the housing 22*b* includes a relatively rigid portion that securely retains the electronic components, and a more resilient portion which functions as an outer layer to provide shock absorption features in the event the activity monitoring device 20*b* is dropped, falls, or otherwise withstands an amount of force.

It will be recognized that in other embodiments, further activity monitoring devices may be provided in any of various different configurations to be worn on any of various locations on the body of the user, such as via a module that clips on to clothing, is worn on a chest strap, fits in a pocket of the user, and/or is incorporated into a garment other than a shoe. Additional or alternative examples of activity monitoring devices include those sold under the trademarks FITBIT®, JAWBONE®, POLAR®, SAMSUNG®, APPLE® and UNDER ARMOUR®.

As shown in FIG. 2, the activity monitoring device(s) 20*a*, 20*b* include electronic circuitry comprising, one or more sensors 26*a*, 26*b*, a processor 27*a*, 27*b*, a memory 28*a*, 28*b*, and a transmitter/receiver 29*a*, 29*b*. The activity monitoring device(s) 20*a*, 20*b* also include a battery or other power source (not shown) configured to power the various electronic devices within the activity monitoring device(s) 20*a*, 20*b*. In one embodiment, the battery of the activity monitoring device 20*a* is a long life non-rechargeable battery designed to last longer than the expected life of the shoe 12. In one embodiment, the battery of the activity monitoring device 20*b* is a rechargeable battery. In this embodiment, the activity monitoring device 20*b* may be placed in or connected to a battery charger configured for use with the activity monitoring device 20*b* in order to recharge the battery.

With continued reference to FIGS. 1-2, the activity monitoring device 20*b* may also include other features visible on the housing 22*b*, such as buttons 23, a display screen 24, one or more connection ports (not shown), or other input/output hardware and software that operate in conjunction with an I/O interface 25. In the embodiment shown, the buttons 23 comprise tactile buttons, switches, and/or toggles. However, in other embodiments, the buttons 23 may also comprise capacitive or resistive touch sensor. The display screen 24 may vary based on the type of device. For example, in the embodiment shown, the display screen 24 comprises an LCD or LED screen that provides performance metric information (e.g., time, distance, pace, heart rate, progress toward a goal, or some combination thereof, etc.), notifications, text messages, caller ID, etc. to the user. In some embodiments, the display screen 24 is a touch screen display that allows the user to provide inputs to the I/O interface 25 via virtual buttons or other interfaces on the touch screen. Alternatively, in one embodiment, the display screen 24 may simply be one or more colored lights and/or flashing patterns configured to communicate information to the user (e.g., progress towards a goal or other performance metric). The connection ports may be used to connect the activity monitoring device 20*b* to a power source or to share data with other electronic devices. It will be appreciated that in some embodiments, the activity monitoring device 20*a* may include similar buttons, displays, and connection ports (not shown).

The sensors 26*a*, 26*b* of the activity monitoring device 20*a*, 20*b* may comprise any of various devices configured to collect the fitness data, including step data, stride length data, stride cadence data, pronation/supination angle data, ground contact time data, foot strike force/direction data, other motion data, distance traversal data, pace data, GPS data, altitude data, heart rate data, breathing data, environmental/positional data, and/or any of various other types of fitness data that may be relevant to determining activities of the wearer. In at least one embodiment, the sensors 26*a* of the activity monitoring device 20*a* include a 3-axis accelerometer configured to detect the motions of the wearer during running or walking, in particular the user's gait or form while running or walking. Of course, it will be recognized by those of ordinary skill in the art that numerous other sensors may be used, depending on the type of activity the respective activity monitoring device 20a, 20b is designed to detect.

With continued reference to FIG. 2, the processor 27a, 27b may be any of various microprocessors as will be recognized by those of ordinary skill in the art. The processor 27a, 27b is configured to receive data signals from the sensors 26a, 26b, and other component parts of the respective activity monitoring device 20a, 20b (such as data entered via the I/O interface 25), and process such signals. The processor 27a, 27b is connected to the respective memory 28a, 28b and the respective transmitter/receiver 29a, 29b, and may deliver processed data to one or both of the respective memory 28a, 28b and the respective transmitter/receiver 29a, 29b. Additionally, the processor 27a, 27b may perform some processing on the received data prior to delivery thereof to the respective memory 28a, 28b or the respective transmitter/receiver 29a, 29b. For example, the processor 27a, 27b may associate the fitness data with a particular time, day, user (in the instance that the device is configured to collect data relating to more than one user), and/or event. The processor 27b is also connected to the I/O interface 25, and may send signals to the I/O interface 25 which results in illumination of the display screen 24 in order to provide text and/or image based messages or otherwise communicate to the user The memory 28a, 28b is configured to store information, including both data and instructions. The data may be retrieved from the processor 27a, 27b and generally includes fitness data, but may also include various types of operational data that may be ancillary to the basic operation of the respective activity monitoring device 20a, 20b. The instructions which are stored at the memory 28a, 28b generally include firmware and/or software for execution by the processor 27a, 27b, such as a program that controls the settings for the sensors 26a, 26b, a program that controls the output of the display screen 24 on the activity monitoring device 20b, a program that controls the receipt of information via the sensors 26a, 26b, a program that controls the transmission and reception of data via the transmitter/receiver 29a, 29b, as well as any of various other programs that may be associated with the respective activity monitoring device 20a, 20b. Such instructions may be present on the device 20a, 20b at the time of manufacture or may be downloaded thereto via well-known mechanisms. The memory 28a, 28b may be of any type capable of storing information accessible by the processor 27a, 27b, such as a memory card, ROM, RAM, write-capable, read-only memories, or other computer-readable medium. The data may be stored in the memory 28a, 28b in a relational database as a table having a plurality of different fields and records, XML documents, or flat files. The data may also be formatted in any computer-readable format such as, but not limited to, binary values, ASCII or Unicode.

The transmitter/receiver 29a, 29b in one embodiment comprises an RF transmitter and receiver configured to transmit and receive communications signals over a short range using a wireless communications technology, such as Wi-Fi or Bluetooth®, using any of various communications protocols, such as TCP/IP. Such transmitter/receivers are well known and will be recognized by those of ordinary skill in the art. The transmitter/receiver 29a, 29b is particularly configured to communicate with the electronic display device 30 when the respective activity monitoring device 20a, 20b is within a given range of the electronic display device 30, and transmit collected fitness data to the electronic display device 30.

Electronic Display Device

With continued reference to FIGS. 1-2, the electronic display device 30 (also referred to herein as a "display device" or a "personal electronic device") generally includes an input/output interface 36, a processor 37, a memory 38, and a transmitter/receiver 39. Additionally, the electronic display device 30 also includes a battery or other power source (not shown) configured to power the electronic components within the electronic display device 30. In at least one embodiment, the electronic display device 30 is a handheld mobile computing device, such as a smartphone. While a smartphone has been shown as the electronic display device 30 in FIGS. 1 and 2, it will be appreciated that the electronic display device 30 may alternatively comprise any number of devices. For example, the electronic display device 30 may be a standalone device, such as a desktop PC, and/or smart television. Alternatively, the electronic display device 30 may be any type of portable or other personal electronic device such as a watch, tablet computer, laptop computer, and/or any of various other mobile computing devices. As will be recognized by those of ordinary skill in the art, the components of the electronic display device 30 may vary depending on the type of display device used. Such alternative display devices may include much (but not necessarily all) of the same functionality and components as the electronic display device 30 shown in FIGS. 1 and 2, as well as additional functionality or components necessary for proper functioning thereof (not shown).

The I/O interface 36 of the electronic display device 30 includes software and hardware configured to facilitate communications with the one or more activity monitoring devices 20 and/or communications to the user him/herself. The hardware includes a display screen 34 configured to visually display graphics, text, and other data to the user. The hardware may also include a microphone and/or speakers to facilitate audio communications with the user and/or verbal entry of commands to the device 30. In at least one embodiment, the display screen 34 is a touch screen display that allows the user to see data presented on the display screen 34 and input data into the electronic display device 30 via a virtual keyboard or other interface on the touch screen. However, other means for receiving user input, such as a physical keyboard, may also be provided with equal success.

The processor 37 of the electronic display device 30 may be any of various processors as will be recognized by those of ordinary skill in the art. The processor 37 is connected to the I/O interface 36, the memory 38, and the transmitter/receiver 39, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 38 is configured to store information, including both data and instructions. The data may be, for example, fitness data as discussed above, which may be related to the activities, workouts, health and fitness profile, etc. of the user, along with other operational data that may be ancillary to the basic operation of the electronic display device 30 and any applications retained on the electronic display device 30. The instructions which are stored at the memory 38 generally include firmware, an operating system, and/or other software for execution by the processor 37, such as one or more programs that control the settings for the electronic display device, one or more programs that control the output of the display screen 34 on the electronic display device 30, one or more programs that control various applications on the electronic display device 30, one or more programs that control the transmission and reception of data via the transmitter/receiver 39, as well as any of various other programs that may be associated with the electronic display device 30. In at least one embodiment, the instructions stored in the memory 38 include a client-side activity tracking application, discussed in greater detail below, which is executed by the processor 37 to process fitness data and present the fitness data in a graphical format on the display screen 34. The memory 38 may be of any type of device capable of storing information accessible by the processor, such as a memory card, ROM, RAM, write-capable memories, read-only memories, hard drives, discs, flash memory, or any of various other computer-readable medium serving as data storage devices, as will be recognized by those of ordinary skill in the art.

The transmitter/receiver 39 is, in one embodiment, an RF transmitter and receiver configured to transmit and receive communications signals using a wireless communications technology, such as Wi-Fi or Bluetooth®, using any of various communications protocols, such as TCP/IP. Such transmitter/receivers are well known and will be recognized by those of ordinary skill in the art. The transmitter/receiver 39 is particularly configured to communicate with a transmitter/receiver 29a, 29b of the activity monitoring device(s) 20a, 20b. In at least one embodiment, the transmitter/receiver 39 is configured to allow the electronic display device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

As discussed above, in at least some embodiments, the electronic display device 30 also functions as a further activity monitoring device and collects certain fitness data independent of the dedicated activity monitoring devices 20a, 20b. Particularly, in at least one embodiment, the electronic display device 30 includes a GPS receiver 31 configured to record a global position of the user during an activity or workout. Additionally, in some embodiments, the electronic display device 30 also includes sensors, such as a 3-axis accelerometer, altimeter, etc. (not shown), configured to record fitness data during an activity or workout.

In at least one embodiment, the electronic display device 30 includes a camera 33 having at least one photo-sensitive element configured to capture an image and/or video of the surroundings. The processor 37 is configured to operate the camera 33 to capture the image and/or video, to receive the image and/or video from the camera 33, and to store the image and/or video in the memory 38. A user may initiate capture of the image and/or video by pressing virtual buttons (not shown) on the display screen 34 or by pressing physical buttons (not shown) of the electronic display device 30.

The electronic display device 30 generally includes a protective outer shell or housing 32 designed to retain and protect the electronic components positioned within the housing 32. The housing 32 may comprise any number of shapes, configurations, and/or materials, the description herein being merely exemplary. In at least one embodiment, the housing 32 includes a relatively rigid portion that securely retains the electronic components, and a more resilient portion which functions as an outer layer to provide shock absorption features in the event the device 30 is dropped, falls, or otherwise withstands an amount of force. In embodiments wherein the electronic display device 30 also functions as a further activity monitoring devices, the housing 32 may serve as a common housing for components of the electronic display device 30 and components of the further activity monitoring device.

In at least one embodiment, the instructions stored in the memory 38 of the electronic display device 30 includes a client-side activity tracking application (which may also be referred to herein as the "workout tracking application"), which is executed by the processor 37 to provide a graphical user interface that enables the user to track, view, and manage his or her fitness data. An exemplary client-side activity tracking application will be discussed in further detail below. In some embodiments, the memory 28b of the activity monitoring device 20b may also include instructions corresponding to the client-side activity tracking application, and may work in combination with the electronic display device 30 to provide the features of the client-side activity tracking application.

System Server

With reference to FIG. 2, the remote system server 40. The system server 40 of FIG. 2 is typically provided in a housing, cabinet or the like 42 that is configured in a typical manner for a server or related computing device. The system server 40 includes a processor 47, memory 48, and a network communications module 49. It is appreciated that the embodiment of the system server 40 shown in FIG. 2 is only one exemplary embodiment of a system server 40. As such, the exemplary embodiment of the system server 40 of FIG. 2 is merely representative of any of various manners or configurations of system servers or other data processing systems that are operative in the manner set forth herein.

The processor 47 is operative, configured and/or adapted to operate the system server 40 including the features, functionality, characteristics and/or the like as described herein. To this end, the processor 47 is operably connected to the memory 48 and the network communications module 49. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 48 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 48 is configured to store instructions including a network-side activity tracking application for execution by the processor 47, as well as a database of fitness data 44 and expert fitness data 46 for use by at least the network-side activity tracking application. As discussed in greater detail below, the processor 47 is configured to collect and store fitness data 44 and/or expert fitness data 46 relating to a plurality of workouts of a plurality of users of the fitness tracking system 10.

The network communications module 49 of the system server 40 provides an interface that allows for communication with any of various devices using various means. In particular, the network communications module 49 includes a local area network port that allows for communication with any of various local computers housed in the same or nearby facility. In some embodiments, the network communications module 49 further includes a wide area network port that allows for communications with remote computers over the network 50 (e.g., the Internet). Alternatively, the system server 40 communicates with the network 50 via a modem and/or router of the local area network. In one embodiment, the network communications module is equipped with a Wi-Fi transceiver or other wireless communications device. Accordingly, it will be appreciated that communications with the system server 40 may occur via wired communications or via the wireless communications. Communications may be accomplished using any of various known communications protocols.

The system server 40 may further include a power module (not shown) which is operative, adapted and/or configured to supply appropriate electricity to the system server 40 (i.e., including the various components of the system server 40). The power module may operate on standard 120 volt AC electricity, but may alternatively operate on other AC voltages or include DC power supplied by a battery or batteries.

The system server 40 may be accessed locally by an authorized user (i.e., an administrator or operator). To facilitate local access, the system server 40 may include an interactive user interface (not shown). Via the user interface, an operator may access the instructions, including the network-side activity tracking application, and may collect data from and store data to the memory 48. In at least one embodiment, the user interface may suitably include an LCD touch screen or the like, a mouse or other pointing device, a keyboard or other keypad, speakers, and a microphone, as will be recognized by those of ordinary skill in the art. Accordingly, the user interface is configured to provide an administrator or other authorized user with access to the memory 48 and allow the authorized user to amend, manipulate and display information contained within the memory.

Activity Tracking Application

The client-side activity tracking applications, stored in the memory 38 of the electronic display device 30 and/or the memory 28b of the activity monitoring device 20b, at least includes instructions for enabling a user to track a plurality of performance metrics during an activity or workout. Particularly, the activity tracking application includes instructions for collecting and processing fitness data during an activity or workout to provide various performance metrics to the user. The term "performance metric" as used herein refers to any standard of measurement relevant to an assessment of the performance, fitness, and health of the user during an activity or workout, or series of activities or workouts. In some cases, the raw measured fitness data is processed substantially to provide a performance metric, but in other cases, measured fitness data may simply be organized into a more presentable form to provide the performance metric. Performance metrics can be generally considered a further type of fitness data, as defined above. Some examples of performance metrics include heart rate sensor data expressed as beats per minute during an activity or workout, acceleration data expressed a total number of steps during an activity or workout, GPS data expressed as a total distance traversed during an activity or workout, GPS data expressed as positions over time and/or a route/path of the user during an activity or workout, GPS data expressed as an speed/pace over time or average speed/pace during an activity or workout, GPS data or altimeter data expressed as an elevation over time during an activity or workout, fitness data expressed as an estimated number of calories burned, time data expressed a total amount of time spent during an activity or workout, and fitness data express as a total number of workouts or number of workouts during a particular time period (e.g., workouts per week). Further exemplary performance metrics may include any parameter of fitness data expressed as an average over a particular duration of time (e.g. the duration of the workout), as a data plot over the particular duration of time, as a maximum or minimum over the particular duration of time, as a value for some point in time of particular interest, or as a percentage of a user's health or fitness goal or other standard.

Figure 3:
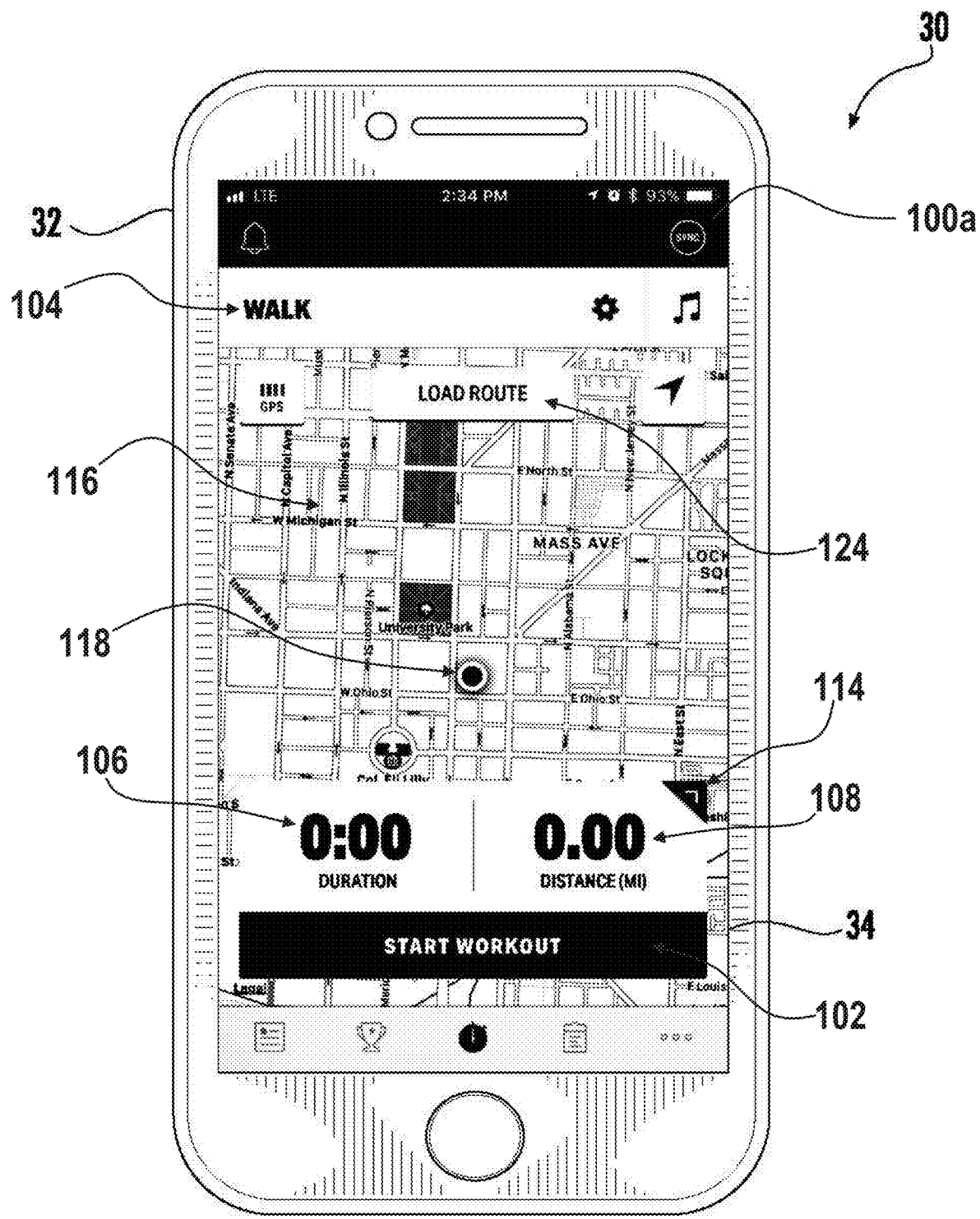
FIG. 3 is a plan view showing an exemplary an activity tracking screen that enables a user to track performance metrics during a workout.

FIG. 3 shows an exemplary embodiment of an activity tracking screen 100a that is displayed on the display screen 34 of the electronic display device 30 to enable a user to track a plurality of performance metrics during an activity or workout. The processor 37 executes instructions of the activity tracking application stored in the memory 38 to display the activity tracking screen 100a on the display screen 34. The activity tracking screen 100a at least includes a start option 102 (e.g., "Start Workout") that enables the user of the electronic display device 30 to initiate collection of fitness data during an activity or workout. Particularly, in response to the user pressing the start option 102, the processor 37 is configured to initiate collection of fitness data by any sensors of the electronic display device 30, such as the GPS receiver 31 and/or initiate reception of fitness data from the activity monitoring device(s) 20a, 20b. In some embodiments, the activity tracking screen 100a includes workout settings option 104 that, when pressed, causes the processor 37 to display an additional menu on the display screen 34 via which the user can choose a type of workout (e.g., walk, run, road cycling, mountain bike, etc.), as well as choose other settings for the workout (e.g., coaching, voice feedback, delay start timer, gear tracking, and other workout settings).

Figure 4:
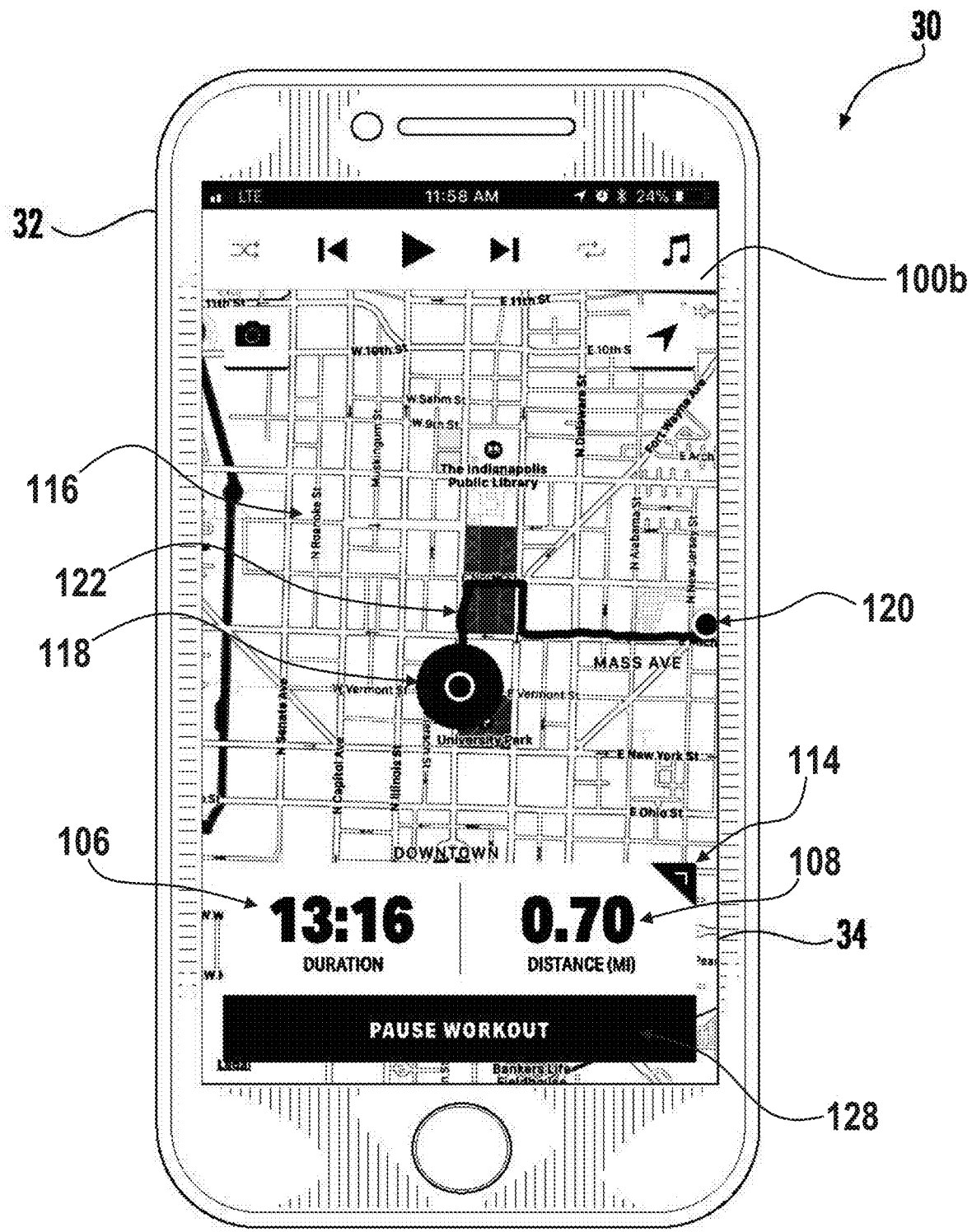
FIG. 4 is a plan view showing an exemplary a real-time tracking screen that enables real-time viewing of certain performance metrics during the workout.

FIG. 4 shows an exemplary embodiment of a real-time tracking screen 100b that is displayed on the display screen 34 of the electronic display device 30 to enable to real-time viewing of certain performance metrics during the activity or workout. Particularly, in at least one embodiment, in response to the user pressing the start option 102 of the activity tracking screen 100a, the processor 37 executes instructions of the activity tracking application to display the real-time tracking screen 100b on the display screen 34, which is different from the activity tracking screen 100a. The real-time tracking screen 100b includes at least one performance metric that is displayed in real time during the activity or workout. Particularly, in the embodiment shown, the real-time tracking screen 100b includes performance metrics 106 and 108 (e.g., a "13:16" value for the "DURATION" performance metric and a "0.70" value for the "DISTANCE (MI)" performance metric). In one embodiment, the real-time tracking screen 100b further includes a expand button 114 that, when pressed by the user, causes the processor 37 to display an expanded view on the display screen 34 that shows values for additional performance metrics in real time during the activity or workout. Additionally, as shown in FIG. 3, the activity tracking screen 100a may also show the metrics 106 and 108 and the expand option 114.

Returning to FIG. 4, the real-time tracking screen 100b includes a map 116 of a geographical area surrounding the electronic display device 30. The processor 37 is configured to receive global position data from a GPS receiver of the electronic display device 30 or of an activity monitoring device(s) 20a, 20b and overlay onto the map 116 in real time a current location 118, a starting location 120, and a route 122 for the current activity or workout. Additionally, as shown in FIG. 3, the activity tracking screen 100a may also show the map 116 and the current location 118. In some embodiments, the activity tracking screen 100a also includes a route option 124 that, when pressed, causes the processor 37 to display an additional menu on the display screen 34 via which the user can select a route for a previous workout. In response to a selection of the previous route, the processor 37 is configured to overlay the previous route (not shown) onto the map 116 of the real-time tracking screen 100b and/or the activity tracking screen 100a.

Finally, the real-time tracking screen 100b includes a pause/end option 128 which enables the user to pause and end tracking of the plurality of performance metrics during the activity or workout. In one embodiment, in response to the user pressing the pause/end option 128, the processor 37 stops collecting fitness data and displays a menu (not shown) on the display screen 34 from which the user can either resume the tracking the workout or end the workout. In at least one embodiment, once the user has ended the workout, the processor 37 is configured to perform additional processing of the collected fitness data to provide additional performance metrics to the user.

In addition to the screens 100a and 100b, which are shown on the display screen 34 of the electronic display device 30, in some embodiments, the user can interact with the activity tracking application via an interface of the activity monitoring device(s) 20a, 20b. Particularly, in at least one embodiment, the user can start and stop the tracking of the activity or workout using an interface of the activity monitoring device 20b. In one embodiment, the user can press one of the buttons 23 of the activity monitoring device 20b to begin tracking a workout. More particularly, in response to the user pressing one of the buttons 23, the processor 27b is configured to initiate collection of fitness data by the sensors 26b of the activity monitoring devices 20b and, optionally, transmit a start command to the electronic display device 30 using the transmitter/receiver 29. In response to receiving the start command, the processor 37 of the electronic display device 30 is configured to initiate collection of fitness data by any sensors of the electronic display device 30, such as the GPS receiver 31 and/or initiate reception of fitness data from other activity monitoring device(s) 20a. Similarly, the user can press one of the buttons 23 of the activity monitoring device 20b to end and/or pause tracking of the workout. Particularly, in response to the user pressing one of the buttons 23 again, the processor 27b is configured to stop collecting fitness data from sensors 26b of the activity monitoring devices 20b and, optionally, transmit a pause and/or end command to the electronic display device 30 using the transmitter/receiver 29. In response to receiving the pause and/or end command, the processor 37 of the electronic display device 30 stops collecting fitness data. In one embodiment, the user taps one of the buttons 23 to pause tracking and either taps one of the buttons 23 again to restart tracking or taps another of the buttons 23 to end tracking. In one embodiment, in response to the ending of the collection of fitness data, the processor 37 of the electronic display device 30 is configured to operate the transmitter/receiver 39 to transmit the fitness data to the system server 40 for processing.

Figure 5:
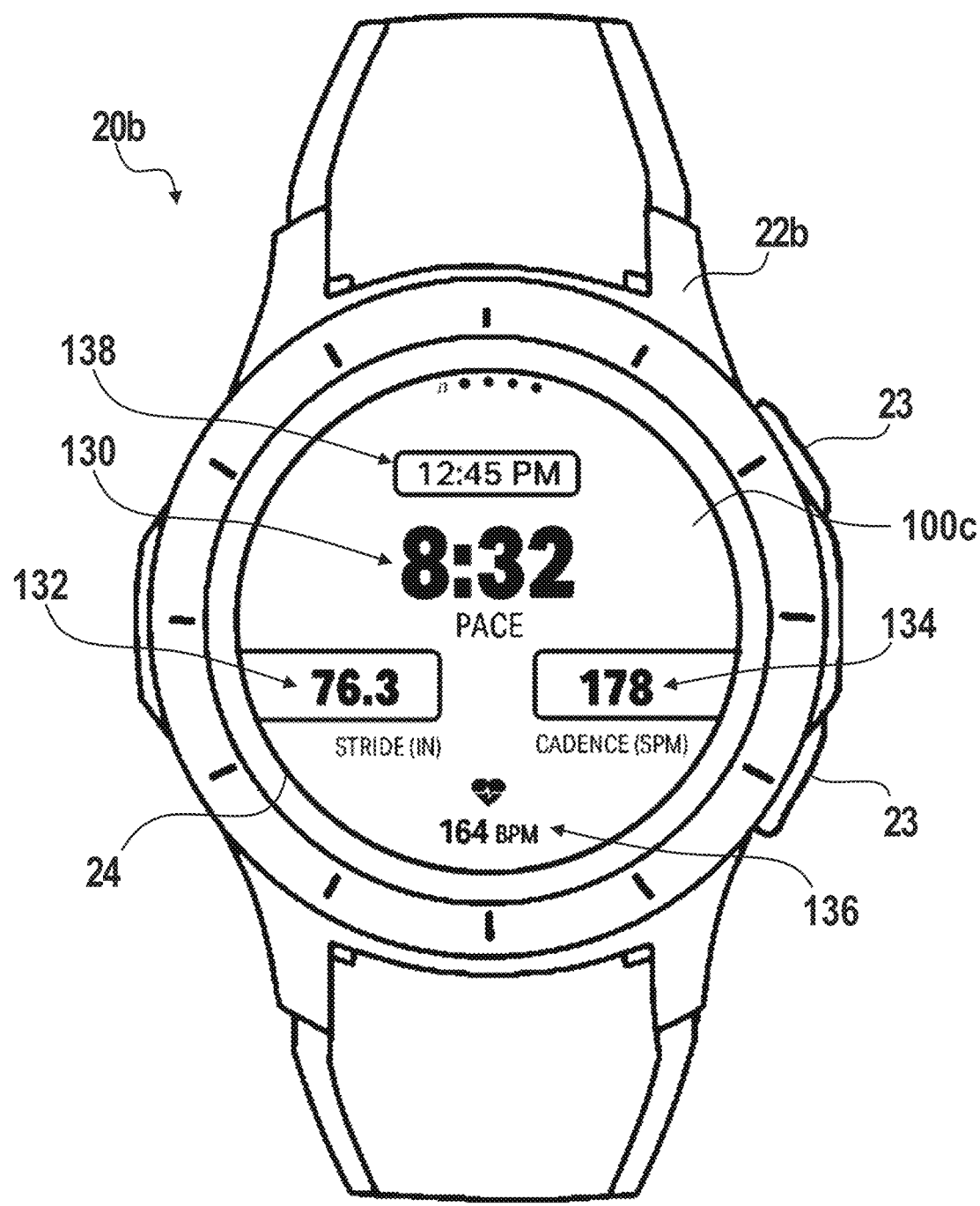
FIG. 5 is a plan view showing a further exemplary a real-time tracking screen that enables real-time viewing of certain performance metrics during the workout.

FIG. 5 shows an exemplary embodiment of a real-time tracking screen 100c that is displayed on the display screen 34 of the activity monitoring device 20b to enable to real-time viewing of certain performance metrics during the activity or workout. Particularly, in response to the user pressing the start option 102 of the activity tracking screen 100a or in response to the user pressing one of the buttons 23, the processor 27b executes instructions of a client-side activity tracking application to display the real-time tracking screen 100c on the display screen 34. The real-time tracking screen 100c includes at least one performance metric that is displayed in real time during the activity or workout. Particularly, in the embodiment shown, the real-time tracking screen 100c includes performance metrics 130, 132, 134 and 136 (e.g., a "8:32" value for the "PACE" performance metric, a "76.3" value for the "STRIDE (IN)" performance metric, a "178" value for the "CADENCE (SPM)" performance metric, and a "164" value for the "BPM" or heart rate performance metric). In one embodiment, the real-time tracking screen 100c further includes a clock 138 that shows a current time of day or a current time since a start of the activity or workout.

Methods for Gait Coaching

Methods for operating the fitness tracking system 10 are described below. In particular, methods of operating the electronic display device 30 and/or the activity monitor device(s) 20a, 20b to provide running gait coaching. In the description of the methods, statements that a method is performing some task or function refers to a controller or general purpose processor executing programmed instructions stored in non-transitory computer readable storage media operatively connected to the controller or processor to manipulate data or to operate one or more components in the fitness tracking system 10 to perform the task or function. Particularly, the processor 37 of the electronic display device 30, the processor 47 of the system server, and/or the processor 27a, 27b of the activity monitoring device(s) 20a, 20b above may be such a controller or processor. Alternatively, the controller or processor may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Method of Modeling Ideal Gait Metrics

FIG. 6 shows a logical flow diagram for a method 200 of generating a gait metric model for determining an ideal running gait for a user. Particularly, the method 200 provides at least one gait metric model that is used to determine an ideal value for at least one gait metric for a particular user. As used herein, the term "gait metric" is a type of performance metric referring to any standard of measurement relevant to an assessment of a gait or form of a user while running or walking. Exemplary gait metrics may include stride length, stride cadence or frequency, pace, ground contact time, pronation/supination angles, and foot strike forces/directions. The method 200 improves upon the functioning of the processor 47 of the system server 40 and/or the processor 37 of the electronic display device 30 by providing a gait metric model that advantageously incorporates running data from a broad diverse population of users, but also specifically considers running data from expert runners. Particularly, the 'shape' of the gait metric model is determined based on running data from a broad diverse population of users, thereby providing a robust estimation of how pace and physiological characteristics such height, age, weight, and sex influence the value for the at least one gait metric. At the same time, the offset and/or Y-axis intercept of the gait metric model is determined based on expert running data from a more limited set of expert users, thereby providing a better indication of what an optimal and/or efficient value for the at least one gait metric.

The method 200 begins with a step of receiving first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length (block 210). Particularly, with respect to the embodiments described in detail herein, the processor 47 of the system server is configured to execute instructions of the network-side activity tracking application to receive and/or read from the memory 48 fitness data 44 corresponding to a plurality of runs of a plurality of users (which may also be referred to as "run data"), which was received from a plurality of electronic display devices (e.g., the electronic display device 30) and/or activity tracking devices (e.g., the activity tracking devices 20a, 20b). Particularly, as discussed above, the client-side activity tracking application of the electronic display device 30 and/or the activity tracking device 20b enables a user to collect fitness data during an activity, such as running. After a run has been completed, the processor 37 of the electronic display device 30 and/or the processor 27b of the activity tracking device 20b is configured to operate the transmitter/receiver 39 and/or the transmitter/receiver 29b to transmit the fitness data to the system server 40 for processing and storage.

Over time, the processor 47 of the system server 40 is configured to receive, and store in the memory 48, fitness data 44 corresponding to a large number of runs performed by a broad and diverse population of users. For each run, the collected fitness data 44 comprises a pace/speed during the respective run, at least one physiological characteristic of the respective user, and at least one gait metric for the respective run. In at least one embodiment, the at least one physiological characteristic includes a height of the respective user, a sex of the respective user, a weight of the respective user, and/or an age of the respective user. In at least one embodiment, the at least one gait metric is a stride cadence or frequency during the respective run and/or a stride length during the respective run. In further embodiments, the at least one gait metric may include ground contact time and/or foot strike forces/directions.

The method 200 continues with a step of determining regression coefficients for at least one gait metric model by performing a regression of the first historical run data, the at least one gait metric model being configured to output the gait metric given inputs of pace, and the at least one physiological characteristic (block 220). Particularly, the processor 47 of the system server 40 is configured to execute instructions of the network-side activity tracking application to generate at least one gait metric model, equation, and/or function configured to output a target value for a gait metric based on inputs at least including a pace and at least one physiological characteristic. In one embodiment, the at least one gait metric model is configured to output the target value for the gait metric based on inputs at least including a pace, a height, an age, a sex, and a weight. In some embodiments, the at least one gait metric model is configured to output a target value for one of stride length and stride cadence. In some embodiments, the processor 47 is configured to generate a plurality of gait metric models, each configured to output a target value for a different gait metric (e.g., stride cadence, stride, ground contact time, and foot strike forces or directions) based on inputs at least including a pace and at least one physiological characteristic (e.g., height, age, sex, and weight).

The processor 47 is configured to generate the at least one gait metric model based on the fitness data 44 corresponding to a large number of runs performed by a broad and diverse population of users. Particularly, in at least one embodiment, the fitness data 44 includes data corresponding to inputs (e.g., pace, height, age, sex, and weight) and the outputs (e.g., stride cadence, stride, ground contact time, and foot strike forces or directions) of the at least one gait metric model. The processor 47 is configured to perform a regression of the fitness data 44 to determine a plurality of regression coefficients and, optionally, a regression constant. Particularly, in one embodiment, each gait metric model takes the form of equation 1:

$$\text{gait metric} = A^*\text{height} + B^*\text{weight} + C^*\text{sex} + D^*\text{age} + E^*\text{pace} + F^*\text{pace}^2 + G \quad (1),$$

where A, B, C, D, E, and F are regression coefficients and G is a regression constant. We note that, as used herein the term "regression coefficient" refers to a value that is multiplied by a variable input term in the gait metric model and the term "regression constant" refers to a value that is added or subtracted in the gait metric model. Additionally, it will be appreciated that the regression coefficients define the 'shape' of the model, whereas the regression constant defines the offset or so-called 'Y-intercept' of the model. As can be seen in equation 1, the influence of pace on the target value for the gait metric is expressed in a polynomial manner by including both a pace term and a pace$^2$ term. In other embodiments, the influence of other inputs may also be expressed with higher ordered terms or in a polynomial manner.

The processor 47 is configured to determine and store in the memory 48 a set of regression coefficients A, B, C, D, E, and F for each gait metric model. Thus, for example, if the at least one gait metric model includes a stride length model and a stride cadence model, then a unique set of regression coefficients A, B, C, D, E, and F are determined and stored for each gait metric model. Additionally, a value for the regression constant G may also be determined in the regression of the fitness data 44. However, as discussed below, this value for the regression constant G will be replaced and/or updated based on a further regression of a more limited set of expert fitness data 46.

The method 200 continues with a step of receiving second historical run data regarding runs of a second plurality of users, the second historical run data including, for each run, the gait metric for the respective run, a pace during the respective run, and the at least one physiological characteristic of the respective user (block 230). Particularly, the processor 47 of the system server 40 is configured to execute instructions of the network-side activity tracking application to receive and/or read from the memory 48 expert fitness data 46 corresponding to a plurality of runs of a plurality of expert users (which may also be referred to as "expert run data"). The plurality of expert users comprises a limited set of runners considered to be experts at running. In one embodiment, the expert fitness data 46 is a manually curated set of fitness data which is similar to the fitness data 44, but corresponds only to runs performed by expert runners. In another embodiment, the expert fitness data 46 is a subset of the fitness data 44 corresponding only to runs performed by users who have recorded a predetermined threshold number of runs (e.g. users who have recorded fitness data for over 100 runs) or have met some other criteria indicative of running expertise. In either case, the expert fitness data 46 differ from the fitness data 44 in that, rather than corresponding to a large number of runs performed by a broad and diverse population of users, the expert fitness data 46 corresponds to a more limited number of runs performed by a more narrowly defined population of expert runners.

The method 200 continues with a step of determining a regression constant for at least one gait metric model by performing a regression of the second historical run data (block 240). Particularly, the processor 47 of the system server 40 is configured to execute instructions of the network-side activity tracking application to modify the at least one gait metric model, discussed above, based on the expert fitness data 46 corresponding to the more limited number of runs performed by the more narrowly defined population of expert runners. Particularly, in at least one embodiment, much like the fitness data 44, the expert fitness data 46 includes data corresponding to inputs (e.g., pace, height, age, sex, and weight) and the outputs (e.g., stride cadence, stride, ground contact time, and foot strike forces or directions) of the at least one gait metric model. The processor 47 is configured to perform a regression of the expert fitness data 46 to determine at least a regression constant for the at least one gait metric model. Particularly, in the exemplary embodiment in which each gait metric model takes the form of equation 1 above, the processor 47 is configured to perform a regression of the expert fitness data 46 to determine the value G. Any initial value for G previous determined based on the previous regression of the fitness data 44 may be ignored and/or updated. The processor 47 is configured to determine and store in the memory 48 a regression constant G for each gait metric model. Thus, for example, if the at least one gait metric model includes a stride length model and a stride cadence model, then a unique value for G is determined and stored for each model.

In at least one embodiment, the processor 47 is configured to transmit the values for the regression coefficients and the regression constant to the electronic display device 30 and/or the activity monitoring device(s) 20a, 20b for usage of the at least one gait metric model thereat.

In summary, the values of the regression coefficients A, B, C, D, E, and F are determined based on a regression of the fitness data 44, whereas the regression constant G is determined based on a regression of the expert fitness data 46. As a result, the 'shape' of each gait metric model is determined based on running data from a broad diverse population of users, thereby providing a robust estimation of how pace and physiological characteristics such height, age, weight, and sex influence the value for the corresponding gait metric (e.g., stride cadence, stride, ground contact time, and foot strike forces or directions). At the same time, the offset and/or Y-axis intercept of each gait metric model is determined based on running data from a more limited set of expert users, thereby providing a better indication of what an optimal and/or efficient value for the at least one gait metric.

It will be appreciated that, if the regression coefficients A, B, C, D, E, and F and the regression constant G were all determined based only on a regression of the fitness data 44, the resulting gait metric model would be one that predicts an expected value for the corresponding gait metric, rather than an optimal and/or efficient value for the corresponding gait metric. Similarly, if the regression coefficients A, B, C, D, E, and F and the regression constant G were all determined based only on a regression of the expert fitness data 46, the resulting gait metric model would lack a robust understanding of how physiological characteristics such height, age, weight, and sex influence the corresponding gait metric, because the more limited set of expert runners are likely to have much less diverse physiological characteristics than the broader population. Accordingly, the gait metric model developed according to the method 200 is clearly improved compared to models developed from a regression of a single data set.

Method of Providing Coaching of Ideal Gait Metrics

Figure 7:
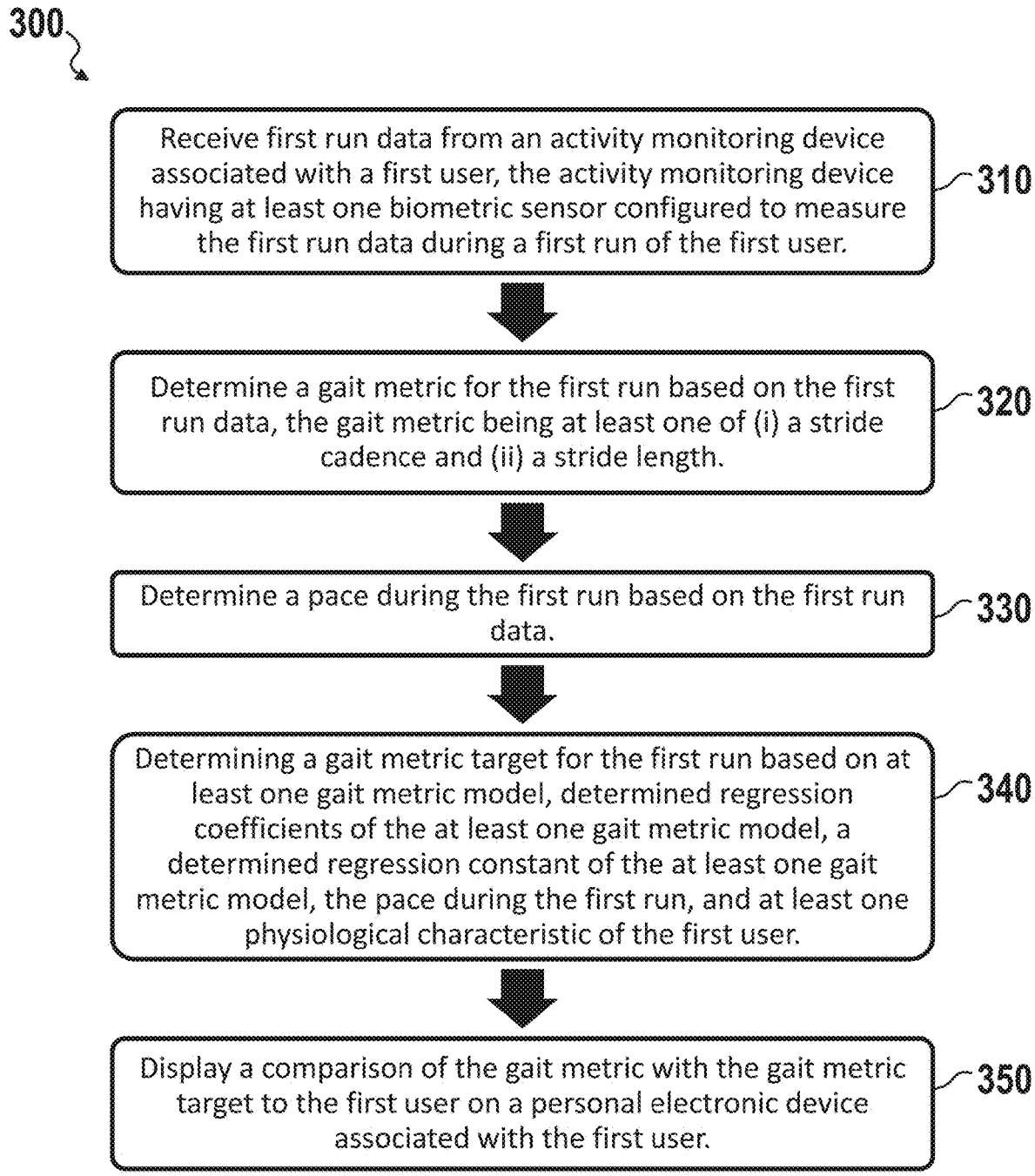
FIG. 7 is a logical flow diagram of a method of processing fitness data corresponding to a run of a user to provide gait coaching for the user.

FIG. 7 shows a logical flow diagram for a method 300 of processing fitness data corresponding to a run of a user to provide gait coaching for the user. Particularly, the method 300 utilizes the gait metric model of the method 200 to determine an ideal value for at least one gait metric for a particular user and to provide comparisons and feedback to the user. The method 300 improves upon the functioning of the processor 37 of the electronic display device 30 and/or the processor 27a, 27b of the activity monitoring device(s) 20a, 20b by advantageously providing the runner with an evaluation of his or her running gait in comparison with an optimal running gait that is determined based on the particular physiological characteristics of the individual and based on the particular pace of the individual run. In this way, the user can be confident in how to modify his or her running gait during his or her next run.

It will be appreciated that, although the method 300 is discussed below primarily with respect to the processor 37 of the electronic display device 30, at least the processor 27b of the activity monitoring device 20b, which is provided in the form of a so-called "smart" watch, may also execute instructions of a client-side activity tracking application to perform some or all of the steps of the method 300. Additionally, in some embodiments, the processor 47 of the system server 40 may execute instructions of a network-side activity tracking application to perform certain steps of the method 300.

The method 300 begins with a step of receiving first run data from an activity monitoring device associated with a first user, the activity monitoring device having at least one biometric sensor configured to measure the first run data during a first run of the first user (block 310). Particularly, with respect to the embodiments described in detail herein, the processor 37 of the electronic display device 30 is configured to execute instructions of the client-side activity tracking application to receive fitness data corresponding to a run of a user from the activity monitoring device(s) 20a, 20b and any sensors of the electronic display device 30. In some embodiments, as discussed above, in response to the user pressing the start option 102 (see FIG. 3) or in response to the user pressing the appropriate button 23 of the activity monitoring device 20b, the processor 37 is configured to initiate collection of the fitness data by any sensors of the electronic display device 30, such as the GPS receiver 31, and/or initiate reception of the fitness data from the activity monitoring device(s) 20a, 20b. In at least one embodiment, the processor 37 is configured to receive the fitness data in real time during the run. In at least one embodiment, the received fitness data includes data such as accelerometer data, step data, stride data, and/or position data, from which a pace of the run and at least one gate metric for the run can be determined.

The method 300 continues with a step of determining a gait metric for the first run based on the first run data, the gait metric being at least one of (i) a stride cadence and (ii) a stride length (block 320). Particularly, the processor 37 is configured to execute instructions of the client-side activity tracking application to calculate a value for at least one gait metric for the run based on the received fitness data corresponding to the run. In at least one embodiment, the processor 37 is configured to calculate an average value for at least one gait metric for the run based on the received fitness data corresponding to the run. In at least one embodiment, the processor 37 is configured to calculate a plurality of timestamped values for at least one gait metric over the duration of the run based on the received fitness data corresponding to the run. In at least one embodiment, the processor 37 is configured to calculate real-time values for the at least one gait metric based on fitness data received in real time during the run. In one embodiment, the processor 37 is configured to calculate the at least one gait metric for the run based on acceleration data or the like received from the sensors 26a of the activity monitoring device 20a. In at least one embodiment, the at least one gait metric is one or more of a stride length over time, an average stride length, a stride cadence over time, and an average stride cadence. In further embodiments, the at least one gait metric may further include ground contact time and/or foot strike forces or directions.

The method 300 continues with a step of determining a pace during the first run based on the first run data (block 330). Particularly, the processor 37 is configured to execute instructions of the client-side activity tracking application to calculate a pace/speed of the run based on the received fitness data corresponding to the run. In at least one embodiment, the processor 37 is configured to calculate an average pace/speed of the run based on the received fitness data corresponding to the run. In at least one embodiment, the processor 37 is configured to calculate a plurality of timestamped values for pace/speed over the duration of the run based on the received fitness data corresponding to the run. In at least one embodiment, the processor 37 is configured to calculate real-time values for pace/speed based on fitness data received in real time during the run. In one embodiment, the processor 37 is configured to calculate the pace of the run based on position data received from the GPS receiver 31. In another embodiment, the processor 37 is configured to calculate the pace of the run based on acceleration data, speed data, position data, or the like received from the sensors 26a of the activity monitoring device 20a.

The method 300 continues with a step of determining a gait metric target for the first run based on at least one gait metric model, determined regression coefficients of the at least one gait metric model, a determined regression constant of the at least one gait metric model, the pace during the first run, and at least one physiological characteristic of the first user (block 340). Particularly, the processor 37 is configured to execute instructions of the client-side activity tracking application to calculate a target value for the at least one gate metric using at least one gait metric model (i.e. one or more of the gait metric models developed in the method 200, above) based on the determined pace and at least one physiological characteristic of the user. Particularly, the processor 37 is configured to receive the calculated regression coefficients (e.g., A, B, C, D, E, and F of equation 1) and regression constant (e.g., G of equation 1) for the at least one gait metric model from the system server 40 and/or read the calculated regression coefficients and regression constant from the memory 38. Using the at least one gait metric model, the processor 37 is configured to calculate a target value for the at least one gait metric based on the determined pace and at least one physiological characteristic of the user. In one embodiment, the at least one physiological characteristic of the user includes a height of the user, an age of the user, a sex of the user, and/or a weight of the user. The at least one physiological characteristic may be stored in the memory 38 in association with a user profile of the user or received from the system server 40. In one embodiment, target value for the at least one gate metric include a target value for stride length and/or a target value for stride cadence. In further embodiments, target value for the at least one gate metric may further include a target value for ground contact time and/or a target value for foot strike force or direction.

As illustrated in more detail below, the target values can take various forms. Particularly, in at least one embodiment, the target values are average target values that are determined using an average pace for the run. In at least one embodiment, the target values are a plurality of timestamped target values over the duration of the run that are determined using a plurality of timestamped pace values over the duration of the run. In at least one embodiment, the target values are real-time target values that are determined using real-time pace values during the run. In at least one embodiment, the processor 37 is configured to determine a target range around the target value for the gait metric. In one embodiment, a size of the range around the target value for the gait metric depends on a confidence factor of the at least one gait metric model. In one embodiment, a size of the range around the target value for the gait metric is predetermined for each type of gait metric model.

The method 300 continues with a step of displaying a comparison of the gait metric with the gait metric target to the first user on a personal electronic device associated with the first user (block 350). Particularly, the processor 37 is configured to execute instructions of the client-side activity tracking application to display a comparison of the determined value for the at least one gait metric with the target value for the at least one gait metric. In at least one embodiment, the processor 37 is configured to display a comparison of the average value for the at least one gait metric for the run with the target average value for the at least one gait metric for the run. In at least one embodiment, the processor 37 is configured to display a comparison in the form of a graph of the plurality of timestamped values for the at least one gait metric over the duration of the run with the plurality of timestamped target values for the at least one gait metric over the duration of the run. In at least one embodiment, the processor 37 is configured to display a comparison of the real-time value for the at least one gait metric during the run with the real-time target value for the at least one gait metric during the run. In at least one embodiment, the processor 37 is configured to display a comparison of the determined value for the at least one gait metric with a predetermined range around the target value for the at least one gait metric. In at least one embodiment, the processor 37 is configured to operate the display screen 34 of the electronic display device to display the comparison. In another embodiment, the processor 27b is configured to operate the display screen 24 of the activity monitoring device 20b to display the comparison.

In at least one embodiment, the processor 37 is configured to enable the user to view the comparison of the determined gait metric value with the gait metric target value after the run has already been performed via a post-workout screen of the client-side activity tracking application.

Exemplary Post-Workout Gait Metric Comparison and Analysis

Figure 8:
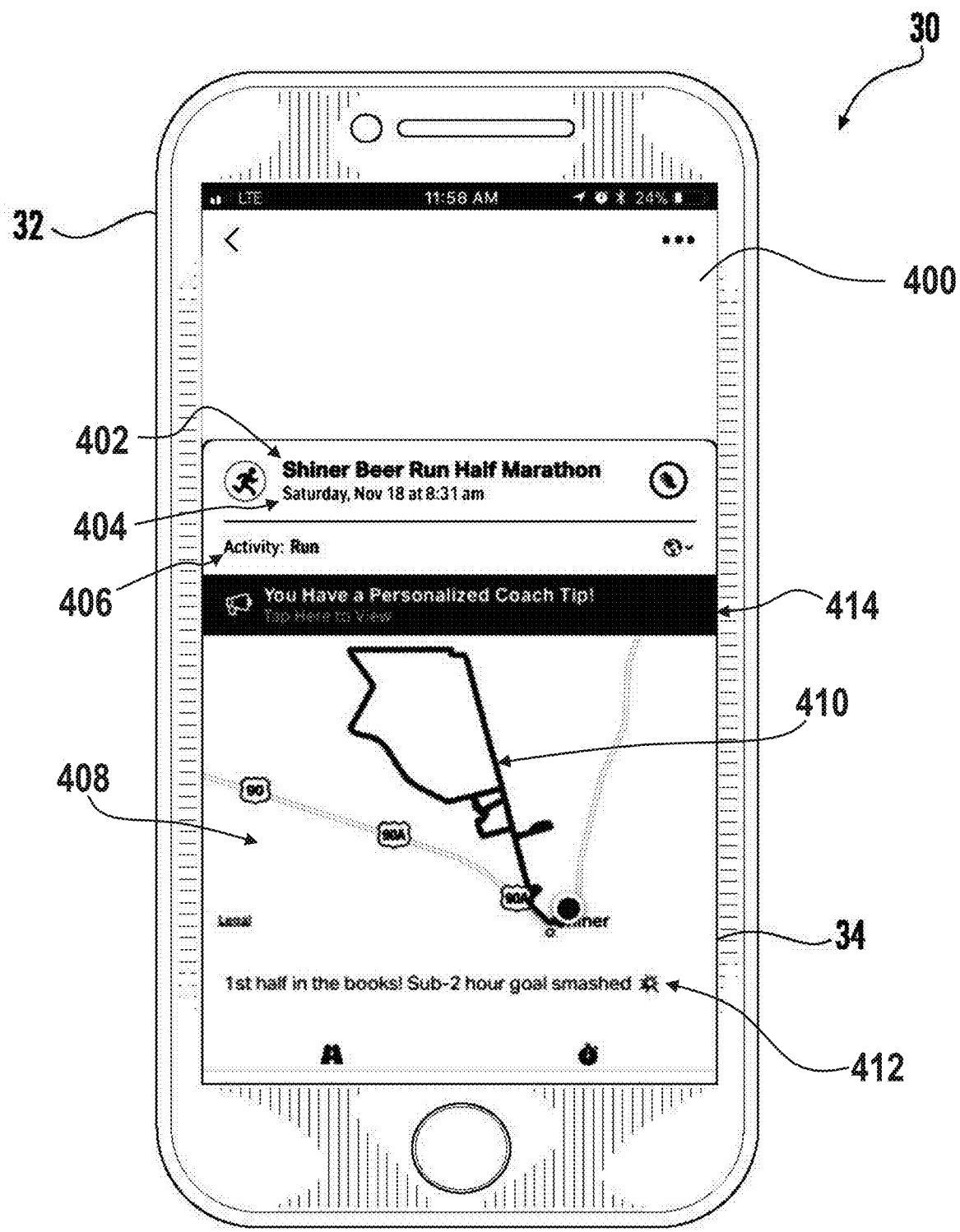
FIG. 8 is a plan view showing an exemplary post-workout screen that displays information regarding a run that has been performed by the user.

FIG. 8 shows an exemplary post-workout screen 400 displayed on the display screen 34 of the electronic display device 30, which displays information regarding a run that has been performed by the user. The post-workout screen 400 includes a title 402 (e.g. "Shiner Beer Run Half Marathon"), which may be generated automatically or chosen by the user, and a time/date 404 (e.g., "Saturday, November 18 at 8:31 am") that indicates the time and date at which the run was performed. The post-workout screen 400 further includes an activity type label 406 (e.g., "Activity: Run") that indicates a type of activity that was performed. The post-workout screen 400 further includes a map 408 showing a route 410 of the run, which was determined by the processor 37 using position data corresponding to the run, such as from the GPS receiver 31. The post-workout screen 400 further includes a notes section 412 having notes or other text regarding the run entered by the user (e.g., "1st half in the books! Sub-2 hour goal smashed"). In many embodiments, the post-workout screen 400 further includes information regarding a plurality of performance metrics for the run (not shown). In one embodiment, the user can view the plurality of performance metrics for the run by scrolling up or down within the post-workout screen 400.

The post-workout screen 400 includes gait coaching banner 414 (e.g., "You Have a Personalized Coach Tip! Tap Here to View"), which can be pressed by the user to display gait coaching information including the comparison of the determined gait metric value with the gait metric target value. Particularly, in response the user pressing or otherwise selecting the coaching banner 414, the processor 37 is configured to operate the display screen 34 to display one or more gait coaching screens of the client-side activity tracking application which compare the user's gait with an ideal gait for the particular user, and provide guidance for how to adjust his or her gait to achieve the ideal gait. It will be appreciated that, in some embodiments, the processor 27b is configured to operate the display screen 24 of the activity monitoring device 20b to display an analogous post-workout screen and/or gait coaching screens.

Figure 9:
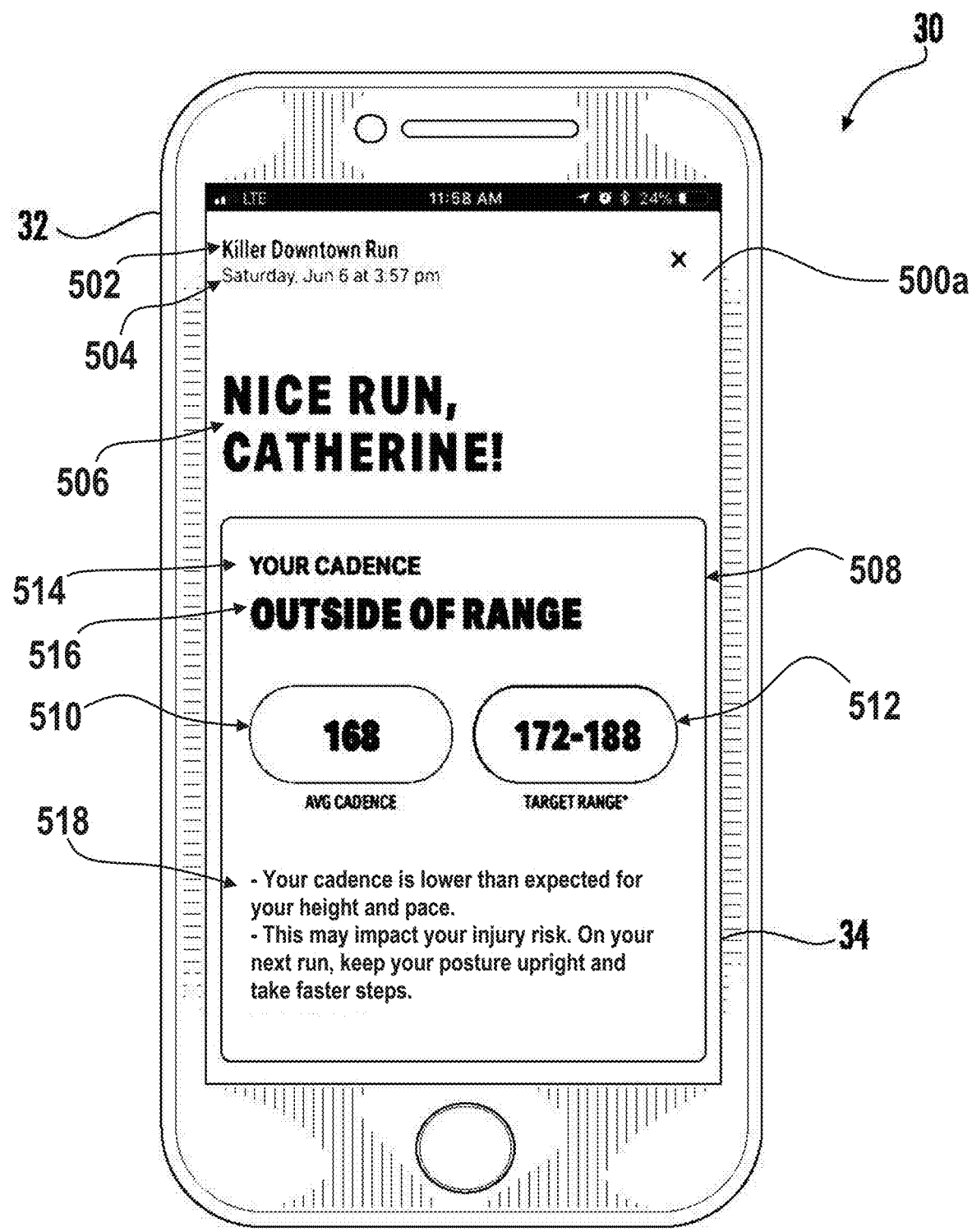
FIG. 9 is a plan view showing an exemplary gait coaching screen that displays a comparison of the user's gait with an ideal gait for the user.

FIG. 9 shows an exemplary gait coaching screen 500a displayed on the display screen 34 of the electronic display device 30, which displays a comparison of the user's gait with an ideal gait for the user. The gait coaching screen 500a includes a title 502 (e.g. "Killer Downtown Run"), which may be generated automatically or chosen by the user, a time/date 504 (e.g., "Saturday, June 6 at 3:57 pm") that indicates the time and date at which the run was performed, an encouragement message 506 (e.g., "NICE RUN, CATHERINE!"), and a gait metric comparison 508.

The gait metric comparison 508 includes a gait metric 510 having a value and label (e.g., a value "168" for the "AVG CADENCE" gait metric) and a gait metric target 512 having a value and label (e.g., a value "172-188" for the "TARGET RANGE"). The gait metric 510 shows the value (e.g., 168 steps per minute) of one of the determined gait metrics for the run (see block 320 of FIG. 7). The gait metric target 512 shows the determined target value (e.g., 180 steps per minute) and/or a predetermined range (e.g., 180±8 steps per minute or 172-188 steps per minute) around the determined target value for the gait metric (see block 340 of FIG. 7). In the illustrated embodiment, the gait metric 510 shows an average value for the run and the gait metric target 512 shows an average target value for the run.

The gait metric comparison 508 further includes a title 514 (e.g., "YOUR CADENCE") and a comparison summary 516 (e.g., "OUTSIDE OF RANGE"). The title 514 indicates which gait metric or gait metrics that are the subject of the gait metric comparison 508. The comparison summary 516 includes a short summary of how the runner's gait metric (e.g., cadence or stride length) compares with the corresponding target value for the gait metric. In one embodiment, the processor 37 is configured to display a first summary (e.g., "OUTSIDE OF RANGE") in response to the determined gait metric (e.g., 168 steps per minute) being outside of a first predetermined range around (e.g., ±8 steps per minute) the determined gait metric target value (e.g., 180 steps per minute). In one embodiment, the processor 37 is configured to display a second summary (e.g., "IN RANGE") in response to the determined gait metric (e.g., 173 steps per minute) being within the first predetermined range (e.g., ±8 steps per minute) around the determined gait metric target value (e.g., 180 steps per minute). In one embodiment, the processor 37 is configured to display a third summary (e.g., "IDEAL RANGE") in response to the determined gait metric (e.g., 178 steps per minute) being within a second predetermined range (e.g., ±3 steps per minute) around the determined gait metric target value (e.g., 180 steps per minute) that is smaller than the first predetermined range.

The gait metric comparison 508 further includes gait metric tips 518 (e.g., "Your cadence is slower than expected for your height and pace." and "This may impact your injury risk. On your next run, keep your posture upright and take faster steps"). In at least one embodiment, the memory 38 stores a plurality of possible messages to include in the gait metric tips 518. In one embodiment, over several runs the processor 37 is configured to select which messages to include in the gait metric tips 518 according to a predetermined sequence. In one embodiment, the processor 37 is configured select at least some of the possible messages to include in the gait metric tips 518 depending on whether the determined gait metric is greater than or less than the determined gait metric target. In one embodiment, the processor 37 is configured select at least some of the possible messages to include in the gait metric tips 518 depending on whether the determined gait metric is within or without the first predetermined range (e.g., ±8 steps per minute) around the determined gait metric target value or within the second predetermined range (e.g., ±3 steps per minute), as similarly described with respect to the comparison summary 516.

In some embodiments, the processor 37 is configured select at least some of the possible messages to include in the gait metric tips 518 depending special circumstances of the run (e.g., the run was on a treadmill or the run was on a hill). For example, since it is known that a treadmill impacts running gait for most runners, the processor 37 is configured select unique messages for the gait metric tips 518 when records a treadmill run (e.g., "It's common for runners to see a decrease in their cadence when on a treadmill, so next time make an extra effort to think 'quick feet!'"). Similarly, if analysis of the run data reveals that the run was performed on a hill, the processor 37 is configured select unique messages for the gait metric tips 518 when records a hill run (e.g., "It's common for a runners to see a decrease in stride length when running up hill, so next time make an extra effort to maintain a consistent stride length when going up a hill.").

In some embodiments, the processor 37 is configured select the messages included in the encouragement message 506, the comparison summary 516, and/or the gait metric tips 518 depending not only the gait metric 510 and gait metric target 512 for the particular run, but also on the performance of the user during a previous run. Particularly, the messages included in the encouragement message 506, the comparison summary 516, and/or the gait metric tips 518 may include a 'follow up' message that relates the user's performance to his or her previous performance. For example, if during the previous run the user's determined gait metric fell below the respective gait metric target range but during this particular run the user's determined gait metric fell within the target range or was closer to the target range, then the encouragement message 506 or the comparison summary 516 might include a message that acknowledges that the user has now achieved his or her target gait metric (e.g., "You increased you cadence. Good Job!"). Similarly, if during the previous run the user's determined gait metric fell within the respective gait metric target range but during this particular run the user's determined fell outside the target range, then the gait metric tips 518 might include a tip that points out that the gait metric is trending in the wrong direction (e.g., "On this run, your stride length is longer than expected for your height and pace. Stride length can vary run to run but, this may impact your injury risk. On your next run, try to match the form of your previous run.").

As discussed above the at least one gait metric model may include individual models for several different gait metrics. Particularly, the gait metric models may include a stride cadence model, a stride length model, a ground contact time model, and a foot strike model. In one embodiment, after each run performed by the user, the processor 37 is configured to select which gait metric to be subject of the gait coaching screen 500a based on a how many runs the user has recorded. For example, in one embodiment, for the first predetermined number of runs (e.g., 15 runs), the gait coaching screen 500a may only relate to stride length or stride cadence, but after the predetermined number of runs, more advanced gait metrics may be introduced, such as ground contact time and foot strike. In one embodiment, over several runs the processor 37 is configured to select which gait metric to be subject of the gait coaching screen 500a according to a predetermined sequence.

Figure 10:
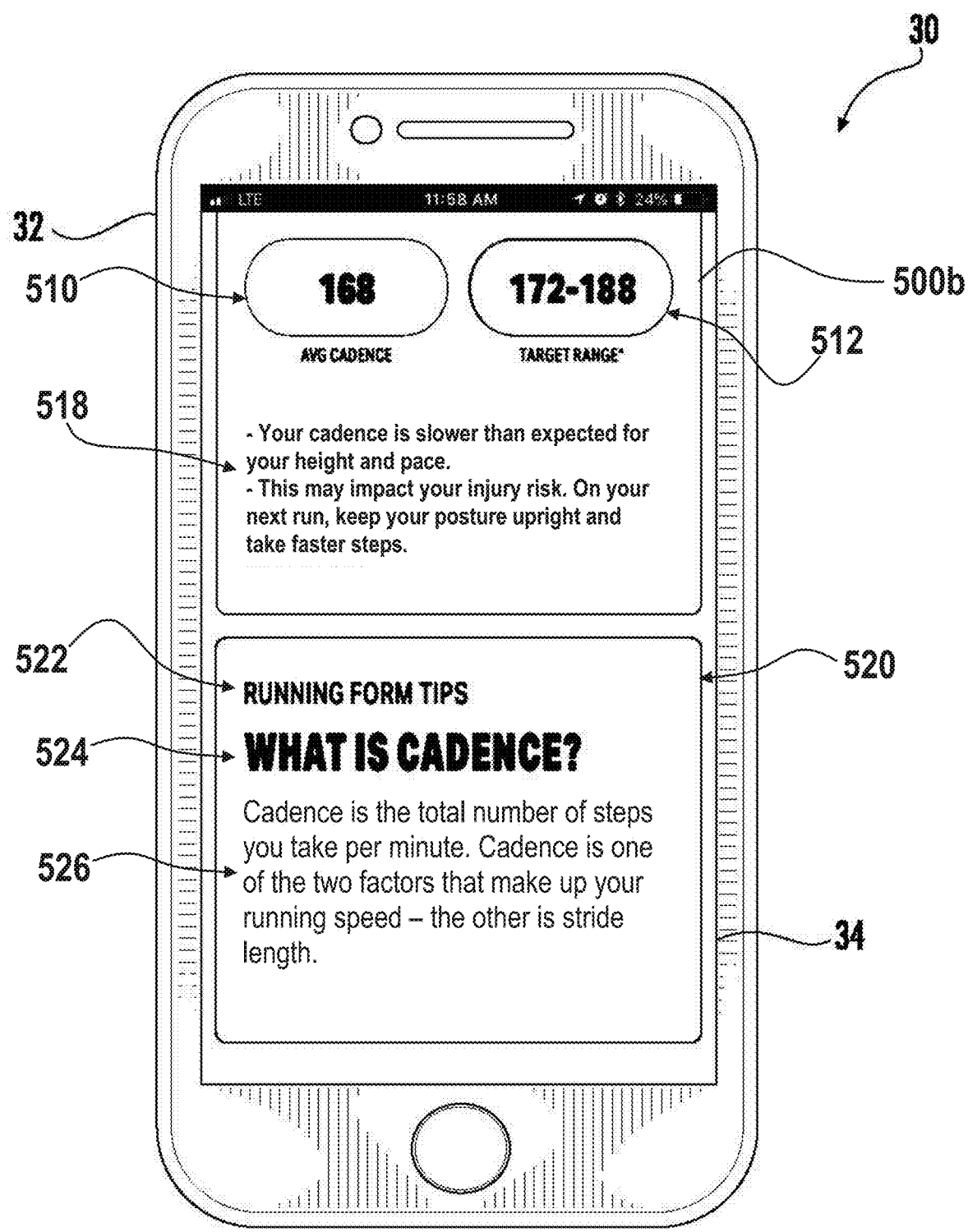
FIG. 10 is a plan view showing an exemplary gait coaching screen that displays general information about the gait metric.

FIG. 10 shows an exemplary gait coaching screen 500b displayed on the display screen 34 of the electronic display device 30, which displays general information about the gait metric. In one embodiment, the user can view the gait coaching screen 500b by scrolling up or down from the gait coaching screen 500a. The gait coaching screen 500b includes general tips section 520. The general tips section 520 includes a section label 522 (e.g., "RUNNING FORM TIPS") and a title 524 (e.g., "WHAT IS CADENCE?") indicating the subject matter of the provided information. The general tips section 520 furthers includes general information 526 which provides general information or advice regarding the particular gait metric or about running form in general (e.g., "Cadence is the total number of steps you take per minute. Cadence is one of the two factors that make up your running speed—the other is stride length"). In at least one embodiment, the memory 38 stores a plurality of possible messages to include in the general information 526. In one embodiment, the processor 37 is configured to select which message to include in the general information 526 based on a how many runs the user has recorded. In one embodiment, over several runs the processor 37 is configured to select which message to include in the general information 526 according to a predetermined sequence.

Figure 11:
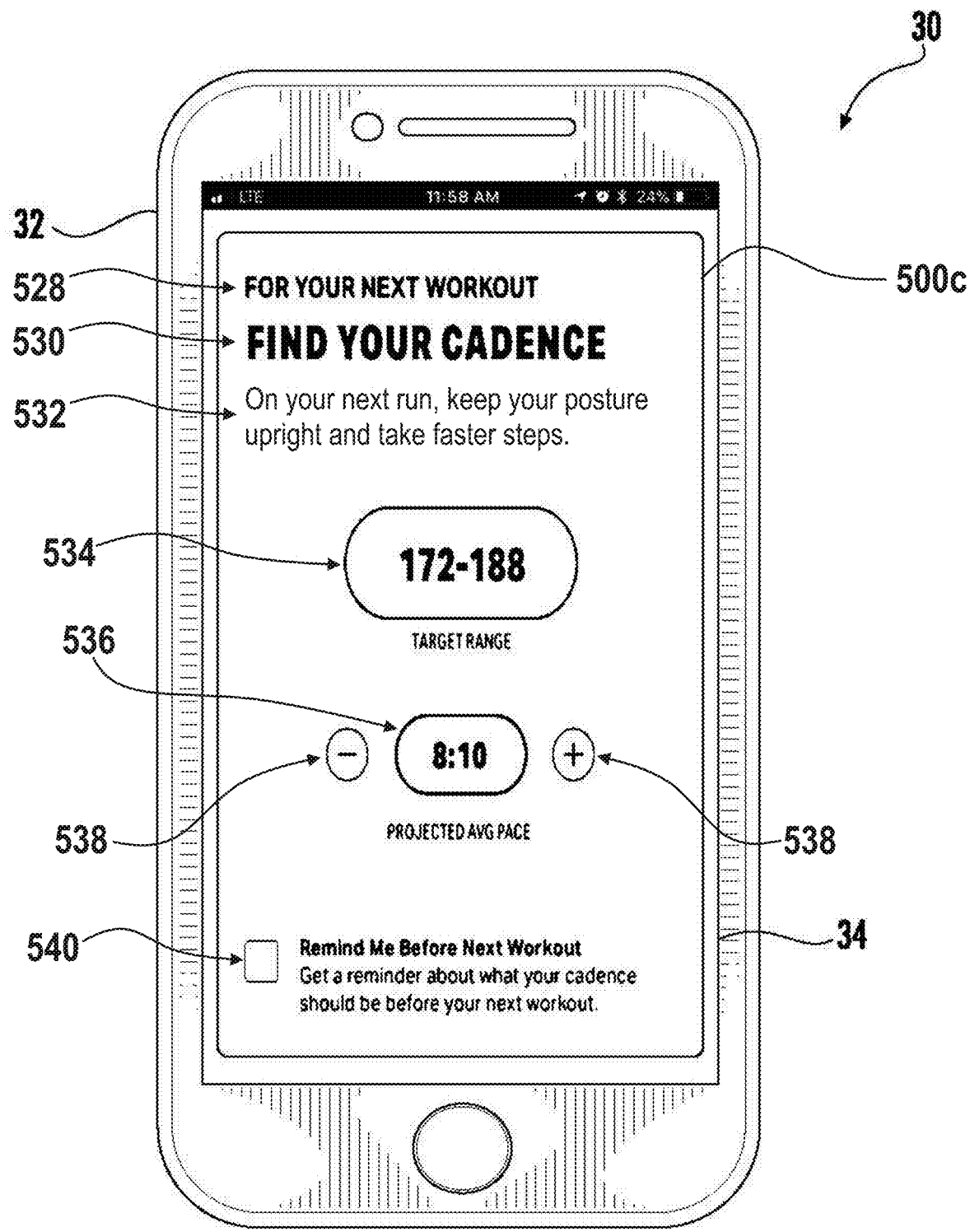
FIG. 11 is a plan view showing an exemplary gait coaching screen that displays gait metric coaching for a next workout.

FIG. 11 shows an exemplary gait coaching screen 500c displayed on the display screen 34 of the electronic display device 30, which displays gait metric coaching for a next workout. In one embodiment, the user can view the gait coaching screen 500c by scrolling up or down from the gait coaching screens 500a or 500b. The gait coaching screen 500c includes a title 528 (e.g., "FOR YOUR NEXT WORKOUT") and subtitle 530 (e.g., "FIND YOUR CADENCE") which indicate the nature of the gait metric coaching for a next workout. The gait coaching screen 500c includes gait metric tips 532, which are similar to the gait metric tips 518 of the gait coaching screen 500a. The gait coaching screen 500c includes gait metric target 534 having a value and label (e.g., a value "172-188" for the "TARGET RANGE"), which is similar to the gait metric target 512 of the gait coaching screen 500a.

The gait coaching screen 500c further includes a projected pace input 536 having a value and label (e.g., a value "8:10" for the "PROJECTED AVG PACE"), as well as adjustment options 538 (e.g., plus and minus buttons) which can be pressed by the user to adjust the value of the projected pace input 536. In response to the user adjusting the value of the projected pace input 536, the processor 37 is configured to recalculate the target value for the gait metric and/or the range around the target value based on the value of the projected pace input 536 in the same manner described above with respect to block 340 of FIG. 7. In this way, the user can better understand how his or her pace affects the target value for the gait metric.

Finally, the gait coaching screen 500c further includes a reminder option 540 having a check box and a description (e.g., "Remind Me Before Next Workout" and "Get a reminder about what your cadence should be before your next workout"). In response to the user selecting the check box of the reminder option 540, the processor 37 is configured to display a reminder which includes the gait metric target 534 to the user before his or her next workout. In one embodiment, the processor 37 is configured to display the reminder in response to the user pressing the start option 102 (see FIG. 3) or in response to the user pressing the appropriate button 23 of the activity monitoring device 20b that initiates tracking of a workout.

In some embodiments, the gait coaching will change over time as the user records more runs and becomes a more experienced runner. Particularly, in one embodiment, if the user has recorded run data for less than a predetermined number of runs (e.g., less than 5 runs), then the processor 37 is configured to display the gait coaching screen 500a having the gait metric comparison 508 in which an average of the gait metric in is displayed in comparison with an average of the gait metric target for the respective run. However, if the user has recorded run data for greater than or equal to the predetermined number of runs, then the processor 37 is configured to display a gait coaching screen having a more detailed comparison of the gait metric with the gait metric target. Alternatively, in some embodiments, the processor 37 is configured to process the run data to determine whether the runner has achieved a stable and/or consistent gait metric. In one embodiment, if the user has not yet achieved a stable and/or consistent gait metric, then the processor 37 is configured to display the gait coaching screen 500a. However, if the user has achieved a stable and/or consistent gait metric, then the processor 37 is configured to display the gait coaching screen having the more detailed comparison of the gait metric with the gait metric target. In at least one embodiment, the more detailed gait metric comparison is in the form of a graph depicting the gait metric in comparison with the gait metric target over time during the respective run.

Figure 12:
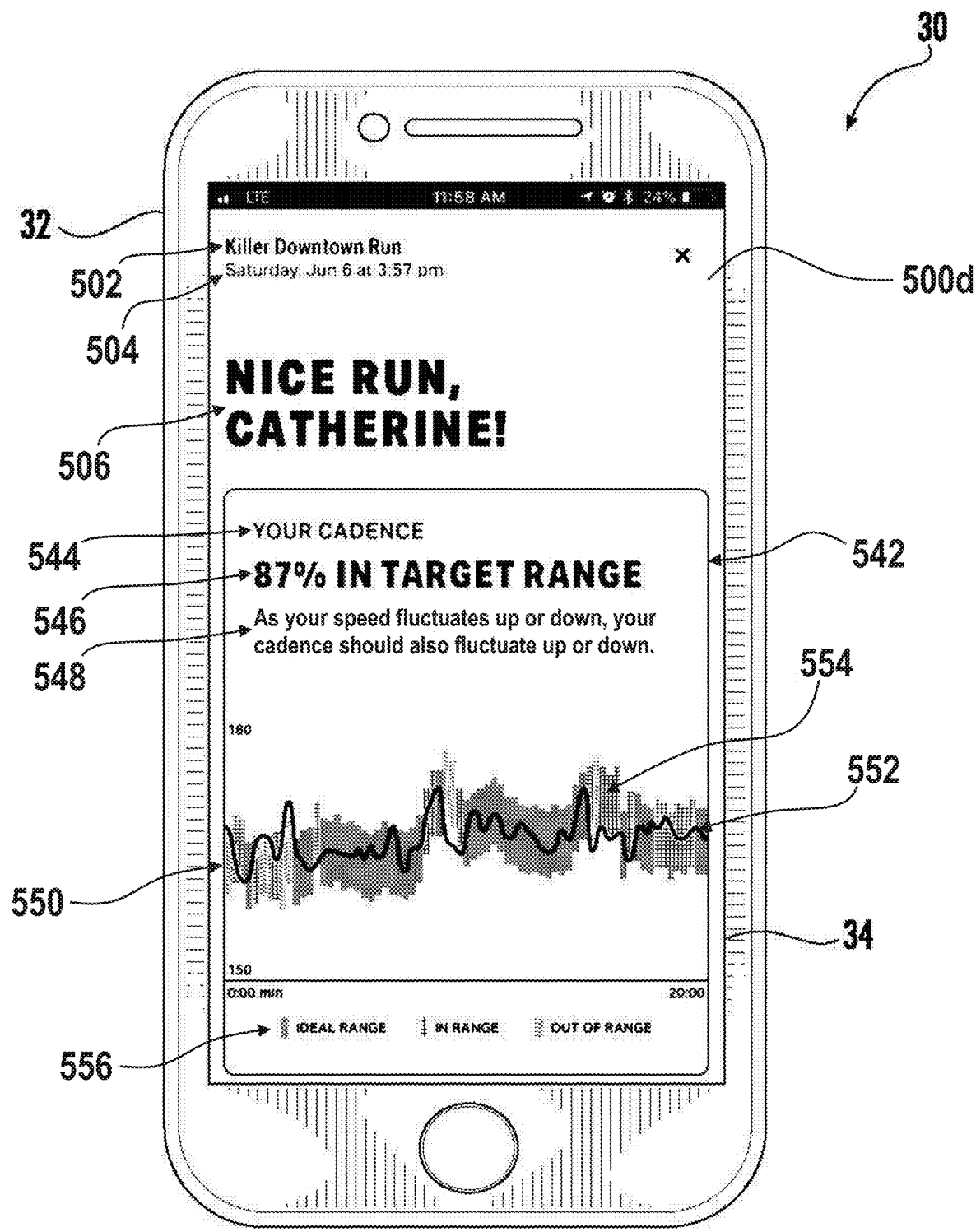
FIG. 12 is a plan view showing an exemplary gait coaching screen that displays a more detailed comparison of the user's gait with an ideal gait for the user.

FIG. 12 shows an exemplary gait coaching screen 500d displayed on the display screen 34 of the electronic display device 30, which displays a more detailed comparison of the user's gait with an ideal gait for the user. Much like the gait coaching screen 500a the gait coaching screen 500d includes the title 502 (e.g. "Killer Downtown Run"), which may be generated automatically or chosen by the user, the time/date 504 (e.g., "Saturday, June 6 at 3:57 pm") that indicates the time and date at which the run was performed, and the encouragement message 506 (e.g., "NICE RUN, CATHERINE!"). However, the gait coaching screen 500d includes a gait metric comparison 542 which is more detailed than the gait metric comparison 508 of the gait coaching screen 500a.

The gait metric comparison 542 includes a title 544 (e.g., "YOUR CADENCE"), a comparison summary 546 (e.g., "87% IN TARGET RANGE"), and a gait metric tips 548 (e.g., "As your speed fluctuates up or down, your cadence should also fluctuate up or down"). The title 514 indicates which gait metric or gait metrics are the subject of the gait metric comparison 542. The comparison summary 546 includes a short summary of how the runner's gait metric (e.g., cadence or stride length) compares with the corresponding target value for the gait metric. In one embodiment, the processor 37 is configured to calculate a percentage of time during the run that the user's gait metric was within a predetermined range of the target value for the gait metric and the comparison summary indicates the percentage (e.g., 87%). The gait metric tips 548, which are similar to those of previously described gait coaching screens, provide coaching or advice regarding the gait metric, such as a message indicating how the gait metric should change over time with changes in pace/speed.

The gait metric comparison 542 includes a graph 550 which depicts a gait metric value 552 over time during the run in comparison with a range 554 around the gait metric target value over time during the run. In one embodiment, the processor 37 is configured to determine, for a plurality of different timestamped gait metric values, whether the gait metric is within or without a first predetermined range (e.g., ±8 steps per minute) around the gait metric target value or within a second predetermined range (e.g., ±3 steps per minute) that is smaller than the first predetermined range.

In one embodiment, the processor 37 is configured to shade or color the range 554 different depending on the whether the gait metric is within or without the first predetermined range or within the second predetermined range. The gait metric comparison 542 includes a legend 556 which indicates the meaning of the shading or coloring of the range 554. In one embodiment, the processor 37 is configured to display a region of the range 554 with a first shading or coloring (e.g., "OUT OF RANGE") in response to the determined gait metric being outside of the first predetermined range around (e.g., ±8 steps per minute) the determined gait metric target value. In one embodiment, the processor 37 is configured to display a region of the range 554 with a second shading or coloring (e.g., "IN RANGE") in response to the determined gait metric being within the first predetermined range (e.g., ±8 steps per minute) around the determined gait metric target value. In one embodiment, the processor 37 is configured to display a region of the range 554 with a third shading or coloring (e.g., "IDEAL RANGE") in response to the determined gait being within the second predetermined range (e.g., ±3 steps per minute) around the determined gait metric target value.

Figure 13:
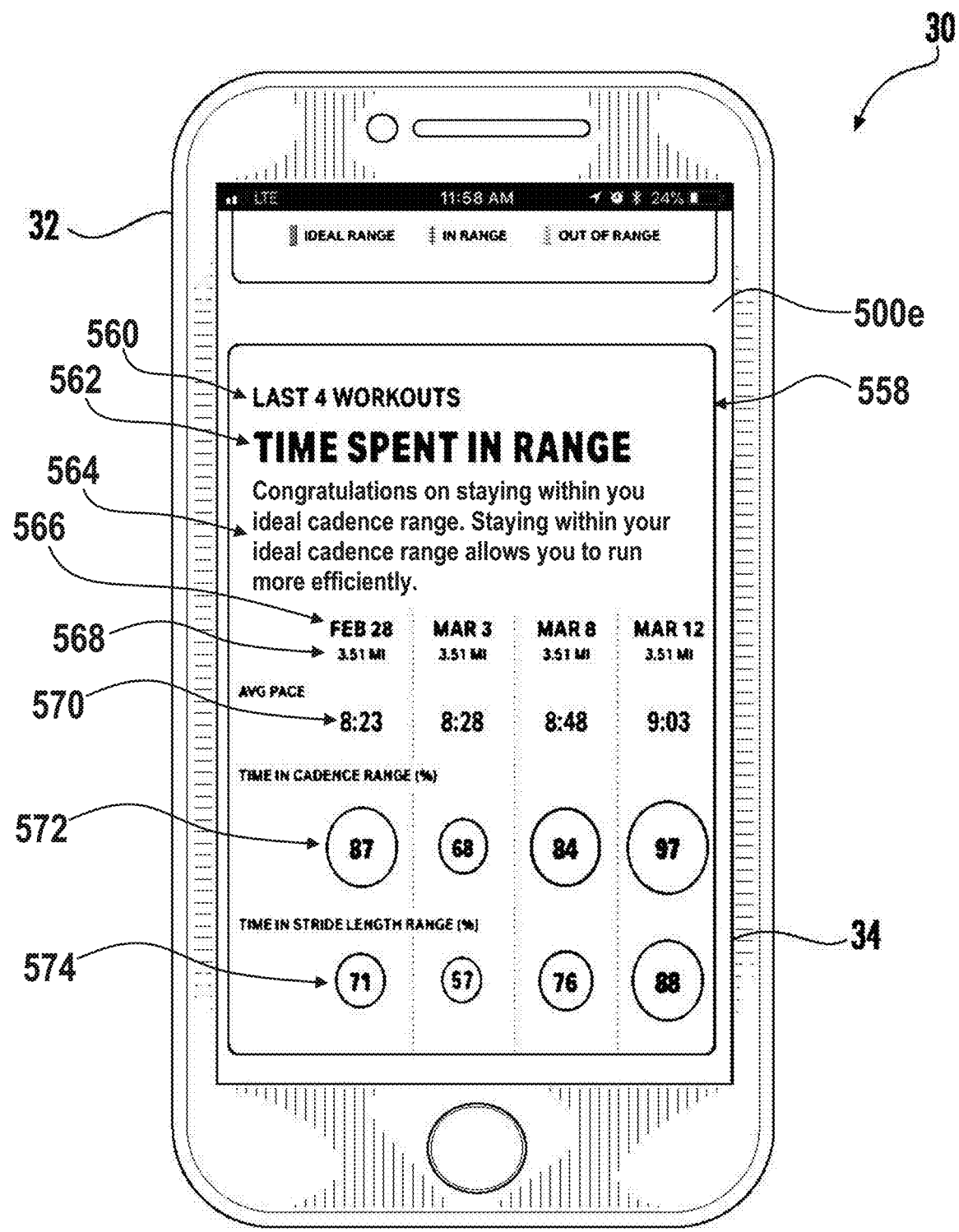
FIG. 13 is a plan view showing an exemplary gait coaching screen that displays a comparison of the user's gait with an ideal gait for the user over several workouts.

FIG. 13 shows an exemplary gait coaching screen 500e displayed on the display screen 34 of the electronic display device 30, which displays a comparison of the user's gait with an ideal gait for the user over several workouts. In one embodiment, the user can view the gait coaching screen 500e by scrolling up or down from the gait coaching screen 500d. The gait coaching screen 500e includes a gait metric comparison 558. The gait metric comparison 558 includes a title 560 (e.g., "LAST 4 WORKOUTS"), a subtitle 562 (e.g., "TIME SPENT IN RANGE"), and a gait metric tips 564 (e.g., "Congratulations on staying within you ideal cadence range. Staying within your ideal cadence range allows you to run more efficiently."). The title 560 and subtitle 562 indicate which workouts and/or gait metrics are the subject of the gait metric comparison 558. The gait metric tips 564, which are similar to those of previously described gait coaching screens, provide coaching or advice regarding the gait metric and/or encouragement and congratulations regarding the user's performance.

The gait metric comparison 558 includes a plurality of columns corresponding to different runs that have been recorded by the user. In one embodiment, the columns correspond to the most recent predetermined number (e.g., 4) of runs. Each column includes a date label 566 (e.g., "FEB 28," "MAR 3," "MAR 8," and "MAR 12") which indicates the date and/or time of the respective run. Each column includes a distance performance metric 568 (e.g., "3.51 MI," "3.51 MI," "3.51 MI," and "3.51 MI") which indicates the distance traveled during the respective run and an average pace performance metric 570 (e.g., "AVG PACE" of "8:23," "8:28," "8:48," and "9:03") which indicates the average pace/speed during the respective run. Each column includes a first comparison 572 of a first gait metric with its respective target range (e.g., "TIME IN CADENCE RANGE (%)" of "87," "68," "84," and "97") and a second comparison 574 of a second gait metric with its respective target range (e.g., "TIME IN STRIDE LENGTH RANGE (%)" of "71," "57," "76," and "88"). In one embodiment, the processor is configured to shade, color, or otherwise mark the comparisons 572 and 574 depending on values of the comparisons (e.g., the percentages, as illustrated). In the illustrated embodiment, each percentage value of the comparisons 572 and 574 is encompassed by a circle having a size that is dependent on the percentage value.

Figure 14:
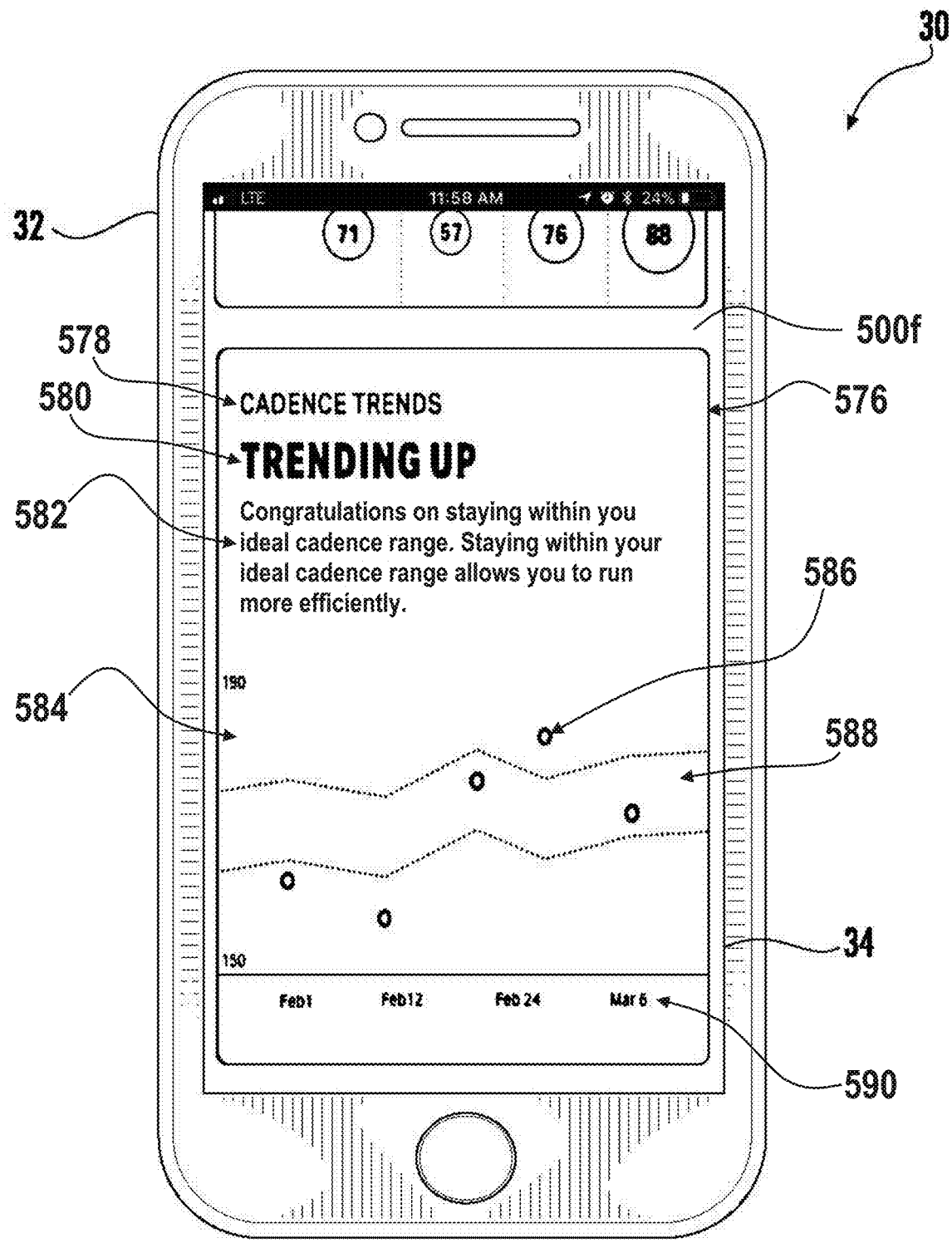
FIG. 14 is a plan view showing a further exemplary gait coaching screen that displays a comparison of the user's gait with an ideal gait for the user over several workouts.

FIG. 14 shows an exemplary gait coaching screen 500f displayed on the display screen 34 of the electronic display device 30, which displays a comparison of the user's gait with an ideal gait for the user over several workouts. In one embodiment, the user can view the gait coaching screen 500f by scrolling up or down from the gait coaching screens 500d or 500e. The gait coaching screen 500f includes a gait metric comparison 576. The gait metric comparison 576 includes a title 578 (e.g., "CADENCE TRENDS"), a comparison summary 580 (e.g., "TRENDING UP"), and a gait metric tips 582 (e.g., "Congratulations on staying within you ideal cadence range. Staying within your ideal cadence range allows you to run more efficiently."). The title 578 indicates which gait metrics or workouts are the subject of the gait metric comparison 576. The comparison summary 580 includes a short summary of how the runner's gait metric (e.g., cadence or stride length) compares with the corresponding target value for the gait metric or how the comparison has changed over several workouts. The gait metric tip 582, which are similar to those of previously described gait coaching screens, provide coaching or advice regarding the gait metric and/or encouragement and congratulations regarding the user's performance.

The gait metric comparison 576 includes a graph 584 which depicts gait metric values 586 for a plurality of workouts in comparison with a range 588 around gait metric target values for a plurality of workouts. In the illustrated embodiment, the gait metric value 586 for each workout date 590 is depicted as a small circle and the bounds of the range 588 are depicted as dashed lines. In one embodiment, the gait metric values 586 and dates 590 correspond to the most recent predetermined number (e.g., 4) of runs.

In some embodiments, gait coaching can be provided to the user in real-time during a run. Particularly, in one embodiment, the processor 27b of the activity monitoring device is configured to provide real-time comparisons and feedback with respect to one or more gait metrics during a run. In some embodiments, the processor 27b of the activity monitoring device 20b is configured to operate the display screen 24 to display the real-time comparisons and feedback. In further embodiments, the processor 27b may be configured to provide the real-time comparisons and feedback to the user audibly using an audio device such as a speaker or headphones worn by the user.

Method of Providing Real-Time Gait Metric Feedback

Figure 15:
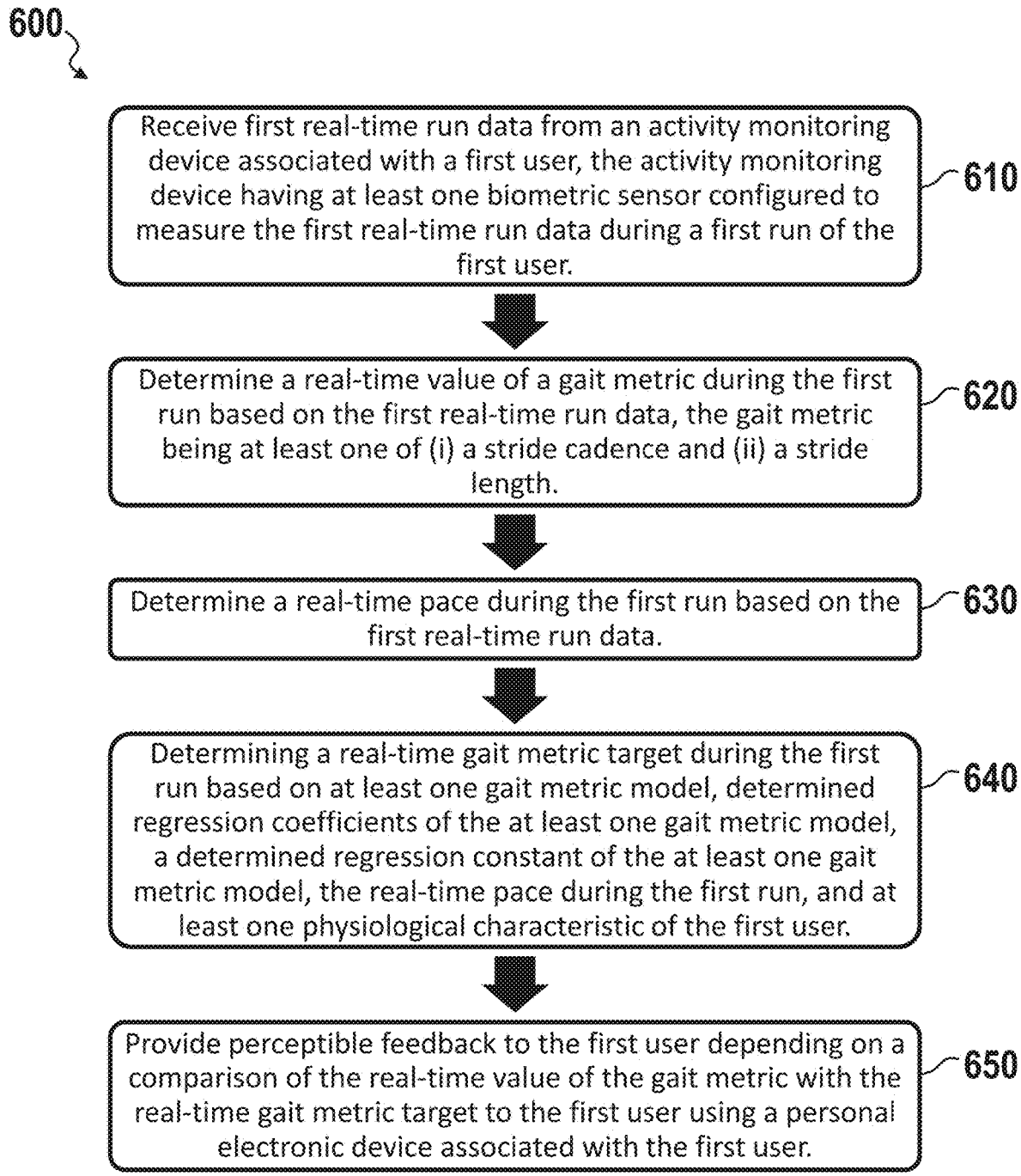
FIG. 15 shows a logical flow diagram for a method of processing real-time fitness data during a run of a user to provide gait coaching for the user.

FIG. 15 shows a logical flow diagram for a method 600 of processing real-time fitness data during a run of a user to provide gait coaching for the user. Particularly, the method 600 utilizes the gait metric model of the method 200 to determine an ideal value for at least one gait metric for a particular user and to provide real-time feedback to the user. The method 600 improves upon the functioning of the processor 37 of the electronic display device 30 and/or the processor 27a, 27b of the activity monitoring device(s) 20a, 20b by advantageously providing the runner with a real-time evaluation of his or her running gait in comparison with an optimal running gait that is determined based on the particular physiological characteristics of the individual and based on the real-time pace during the run. In this way, the user can more easily learn to run with an ideal and efficient gait.

The method 600 begins with a step of receiving first real-time run data from an activity monitoring device associated with a first user, the activity monitoring device having at least one biometric sensor configured to measure the first real-time run data during a first run of the first user (block 610). Next, the method 600 continues with steps of determining a real-time value of a gait metric during the first run based on the first real-time run data, the gait metric being at least one of (i) a stride cadence and (ii) a stride length (block 620) and determining a real-time pace during the first run based on the first real-time run data (block 630). The method 600 continues with a step of determining a real-time gait metric target during the first run based on at least one gait metric model, determined regression coefficients of the at least one gait metric model, a determined regression constant of the at least one gait metric model, the real-time pace during the first run, and at least one physiological characteristic of the first user (block 640). The steps 610, 620, 630, and 640 of the method 600 are essentially similar to the steps 310, 320, 330, and 340 of the method 300 described in detail above, except that the steps are performed in real-time during a run using real-time fitness data. Accordingly, the steps 610, 620, 630, and 640 of the method 600 are not described again in detail. Furthermore, as with the method 300, it will be appreciated that one or both of the processor 37 of the electronic display device 30 and the processor 27b of the activity monitoring device 20b may execute instructions of a client-side activity tracking application to perform some or all of the steps of the method 600. Additionally, in some embodiments, the processor 47 of the system server 40 may execute instructions of a network-side activity tracking application to perform certain steps of the method 600.

The method 600 continues with a step of providing perceptible feedback to the first user depending on a comparison of the real-time value of the gait metric with the real-time gait metric target to the first user using a personal electronic device associated with the first user (block 650). Particularly, the processor 37 of the electronic display device 30 and/or the processor 27b of the activity monitoring device 20b is configured to execute instructions of the client-side activity tracking application to provide real-time perceptible feedback to the user depending on a comparison of the determined value for the at least one gait metric with the target value for the at least one gait metric. In at least one embodiment, the processor 37 is configured to operate the display screen 34 of the electronic display device to display the feedback. In another embodiment, the processor 27b is configured to operate the display screen 24 of the activity monitoring device 20b to display the feedback. In one embodiment, the processor 37 and/or the processor 27b is configured to operate an audio device of one of the devices 30 and/or 20b (not shown), such as a speaker or headphones, to provide the feedback audibly.

In at least one embodiment, the processor 37 and/or the processor 27b is configured to display a comparison of the real-time value for the at least one gait metric during the run with the real-time target value for the at least one gait metric during the run. In at least one embodiment, the processor 37 and/or the processor 27b is configured to display a comparison of the real-time value for the at least one gait metric with a predetermined range around the real-time target value for the at least one gait metric.

In at least one embodiment, the processor 37 and/or the processor 27b is configured to provide a feedback message instructing the user to adjust the gait metric (e.g., stride length or cadence) up or down in response to the real-time value for the at least one gait metric being outside a predetermined range of the real-time target value for the at least one gait metric. In at least one embodiment, the processor 37 and/or the processor 27b is configured to provide a feedback message instructing the user to maintain the real-time target value for the at least one gait metric at one of (i) a defined time during the run and (ii) a defined distance traveled during the run. In at least one embodiment, the processor 37 and/or the processor 27b is configured to determine the defined time during the run and/or the defined distance traveled during the run based on an analysis of fitness data corresponding to previously recorded runs of the user.

Exemplary Real-Time Gait Method Feedback

Figure 16A:
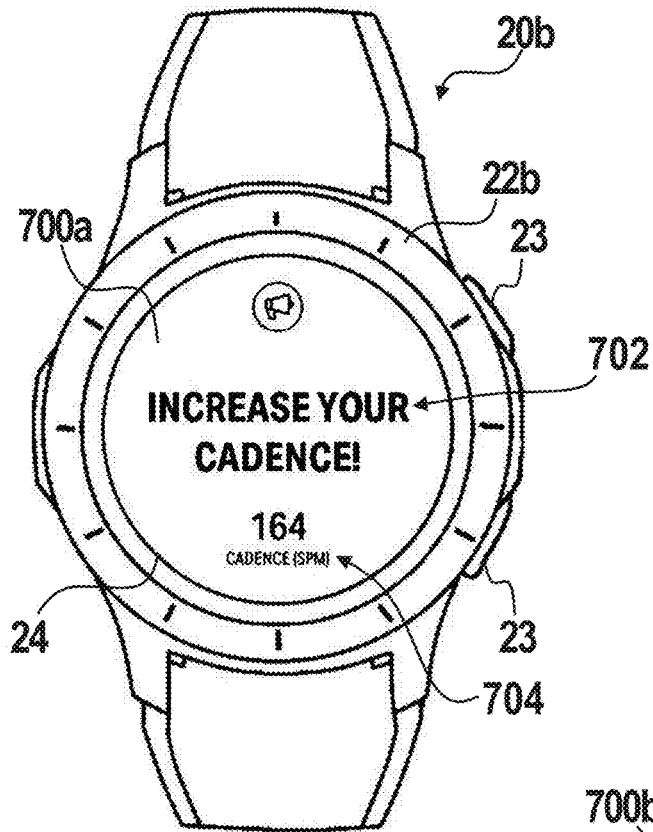
FIG. 16A is a plan view showing an exemplary gait coaching screen that includes real-time feedback regarding the user's gait as compared with an ideal gait for the user.

FIG. 16A shows an exemplary gait coaching screen 700a displayed on the display screen 24 of the activity monitoring device 20b, which includes real-time feedback regarding the user's gait as compared with an ideal gait for the user. The gait coaching screen 700a includes a feedback message 702 (e.g., "INCREASE YOUR CADENCE!") and a real-time gait metric 704 having a value and a label (e.g., a value "164" for the "CADENCE (SPM)" gait metric). In one embodiment, the processor 37 and/or the processor 27b is configured to provide the feedback message 702 in response to the value for the real-time gait metric 704 being less than a lower bound of the predetermined range (e.g., more than 5 steps per minute below) around the real-time target value for the gait metric. In one embodiment, the processor 37 and/or the processor 27b is configured to provide a different feedback message (e.g., "DECREASE YOUR CADENCE!") in response to the value for the real-time gait metric 704 being greater than an upper bound of the predetermined range (e.g., more than 5 steps per minute over) around the real-time target value for the gait metric. In one embodiment, the processor 37 and/or the processor 27b is configured to provide a different feedback message (e.g., "MAINTAIN THIS CADENCE!") in response to the value for the real-time gait metric 704 being within the predetermined range (e.g., within ±8 steps per minute) around the real-time target value for the gait metric. Alternatively, in some embodiments, no feedback message is displayed in response to the value for the real-time gait metric 704 being within the predetermined range around the real-time target value for the gait metric.

Figure 16B:
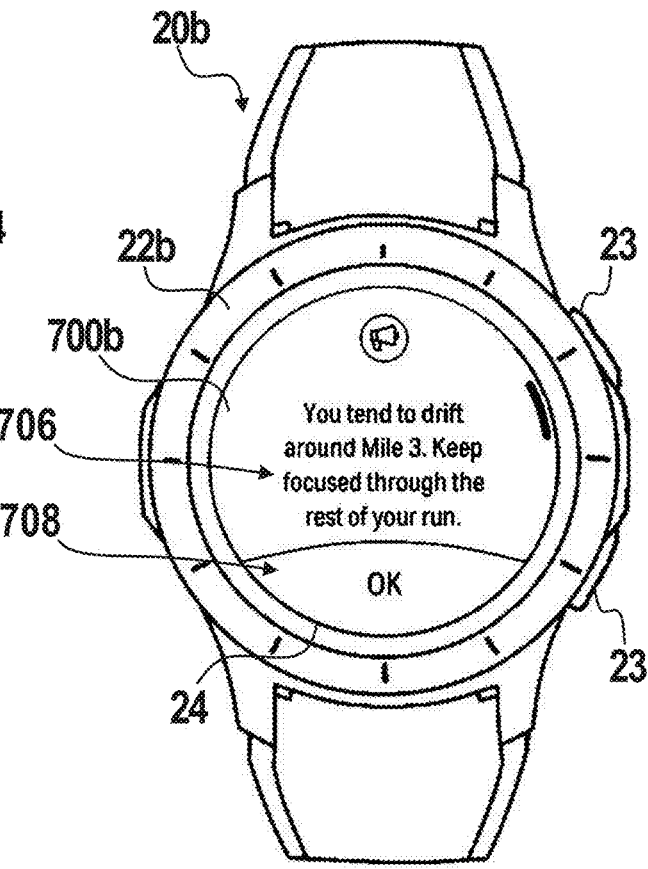
FIG. 16B is a plan view showing a further exemplary gait coaching screen that includes real-time feedback regarding the user's gait as compared with an ideal gait for the user.

FIG. 16B shows a further exemplary gait coaching screen 700b displayed on the display screen 24 of the activity monitoring device 20b, which includes real-time feedback regarding the user's gait as compared with an ideal gait for the user. The gait coaching screen 700b includes a feedback message 706 (e.g., "You tend to drift around Mile 3. Keep focus through the rest of your run") and a dismiss button 708 (e.g., "OK"). In at least one embodiment, the processor 37 and/or the processor 27b is configured to provide the feedback message 706 at a defined time during the run or at a defined distance traveled during the run. In at least one embodiment, the processor 37 and/or the processor 27b is configured to determine the defined time during the run and/or the defined distance traveled during the run based on an analysis of fitness data corresponding to previously recorded runs of the user. For example, if analysis of previous run indicates that the gait metric of the user typically drifts at a particular time or distance traveled (e.g. at mile 3), the processor 37 and/or the processor 27b is configured to display a feedback message reminding the user to maintain the target value for the gait metric a time briefly before the particular time or shortly before the particular distance (e.g., the reminder may be provided at 2.8 miles traveled). As another example, in the case that the user is running a predefined course or route that that he or she has already run before and analysis of previous run on the predefined course or route indicates that the gait metric of the user typically drifts at a particular location or distance on the predefined course or route (e.g. at mile 3 or during a $3^{rd}$ lap) the processor 37 and/or the processor 27b is configured to display a feedback message reminding the user to maintain the target value for the gait metric a time briefly before the particular location or distance on the predefined course or route (e.g., the reminder may be provided at 2.8 miles travel on the route or before the $3^{rd}$ lap).

In one embodiment, during a run, the processor 37 and/or the processor 27b is configured to provide an instruction to the user to maintain the target value for the at least one gait metric during a particular interval of time during the run (herein after referred to as "form intervals"). During the form interval, the processor 37 and/or the processor 27b is configured to monitor whether the real-time value of the at least one gait metric is within the predetermined range of real-time target value for the at least one gait metric. In one embodiment, the processor 37 and/or the processor 27b is configured to provide a feedback message indicating whether the real-time value of the gait metric is within predetermined range during the form interval. In one embodiment, the processor 27b is configured to operate the display screen 24 to display a comparison of the real-time value of the gait metric with the real-time gait metric target during the form interval. These form intervals motivate the user to focus on their running gait/form for a limited interval of time. By instructing the user to focus on their running form during short bursts of time, the user is better able to understand and contrast how it feels to run with an ideal gait and can more easily adopt the ideal gait as his or her normal running form.

Figure 17:
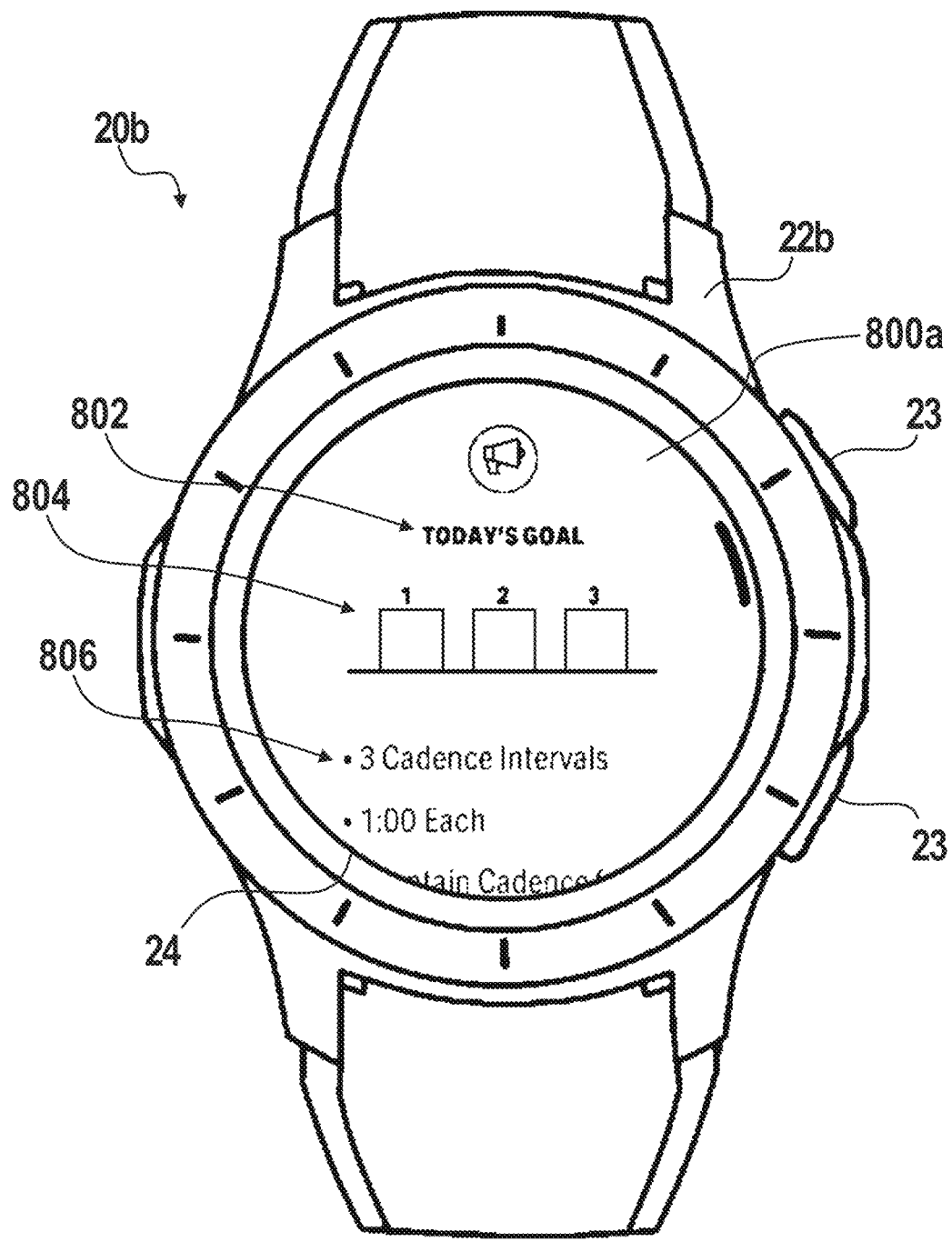
FIG. 17 is a plan view showing an exemplary form interval screen that shows information regarding form intervals to be performed during a run.

FIG. 17 shows an exemplary form interval screen 800a displayed on the display screen 24 of the activity monitoring device 20b, which shows information regarding form intervals to be performed during a run. The form intervals screen 800 includes a title 802 (e.g., "TODAY'S GOAL"), a graphical depiction of a sequence of form intervals 804 (e.g., a time plot showing a chronological sequence of form intervals 1, 2, and 3), and form interval information 806 (e.g., "3 Cadence Intervals" and "1:00 Each"). In one embodiment, the processor 27b is configured to display the form intervals screen 800a in response to the user initiating the tracking of a workout in the various manners discussed above. In one embodiment, the processor 27b is configured to display the form intervals screen 800a during a warm up phase and/or walking phase of the workout, prior to the particular intervals of time during which the form intervals will be performed.

Figure 18A:
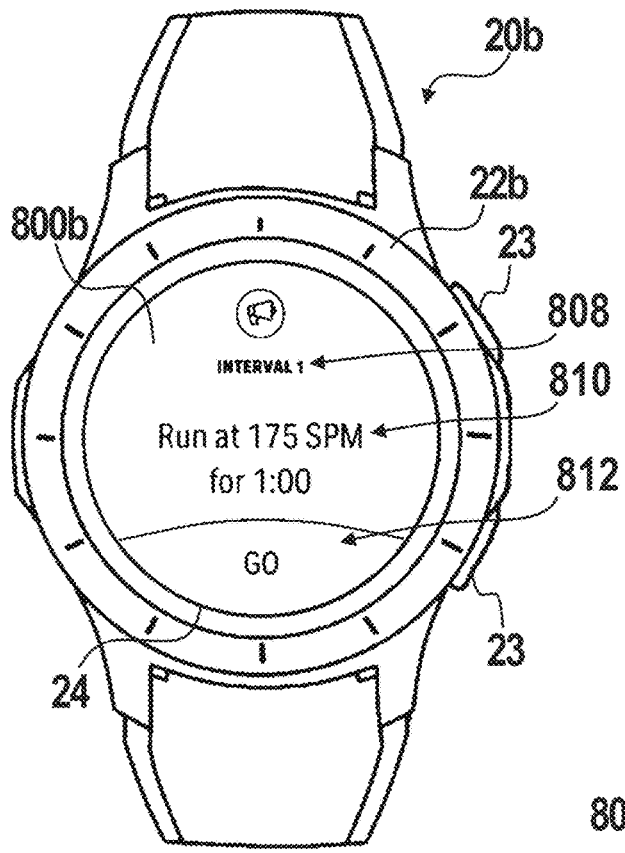
FIG. 18A is a plan view showing an exemplary form intervals screen that shows instructs the user to begin an form interval.

FIG. 18A shows an exemplary form intervals screen 800b displayed on the display screen 24 of the activity monitoring device 20b, which instructs the user to begin an form interval. The form interval screen 800b includes a title 808 (e.g., "Interval 1") indicating which particular form interval in the sequence of form intervals is to be performed, instructions 810 (e.g., "Run at 175 SPM for 1:00") instructing the user maintain a target value for a gait metric for a particular duration of time, and a start button 812 (e.g., "GO") which can be pressed by the user to begin the form interval. In one embodiment, the processor 27b is configured to display the form intervals screen 800b before each form interval is performed. In at least one embodiment, the target value for the gait metric (e.g., 175 steps per minute) corresponding to the form interval depends upon a pace of the user immediately before the start of the form interval. In other embodiments, the target value for the gait metric may be predetermined based on an average pace during previously recorded runs of the user.

Figure 18B:
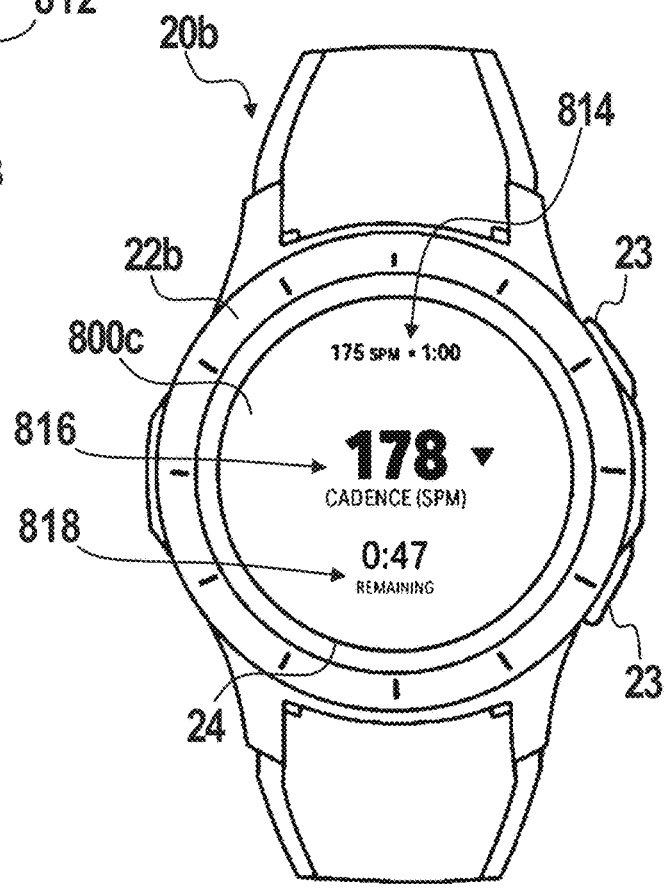
FIG. 18B is a plan view showing an exemplary form intervals screen that shows real-time monitoring of the gait metric during a form interval.

FIG. 18B shows an exemplary form intervals screen 800c displayed on the display screen 24 of the activity monitoring device 20b, which shows real-time monitoring of the gait metric during a form interval. The form interval screen 800c includes a comparison of a target gait metric 814 (e.g., "175 SPM●1:00") and a real-time gait metric 816 (e.g., a value "178" for the "CADENCE (SPM)" gait metric). Additionally, the form interval screen 800c includes a timer 818 (e.g., "0:47 REMAINING") which indicates an amount of time remaining in a particular form interval. In one embodiment, the processor 27b is configured to display the form intervals screen 800b during each form interval that is performed.

Figure 19:
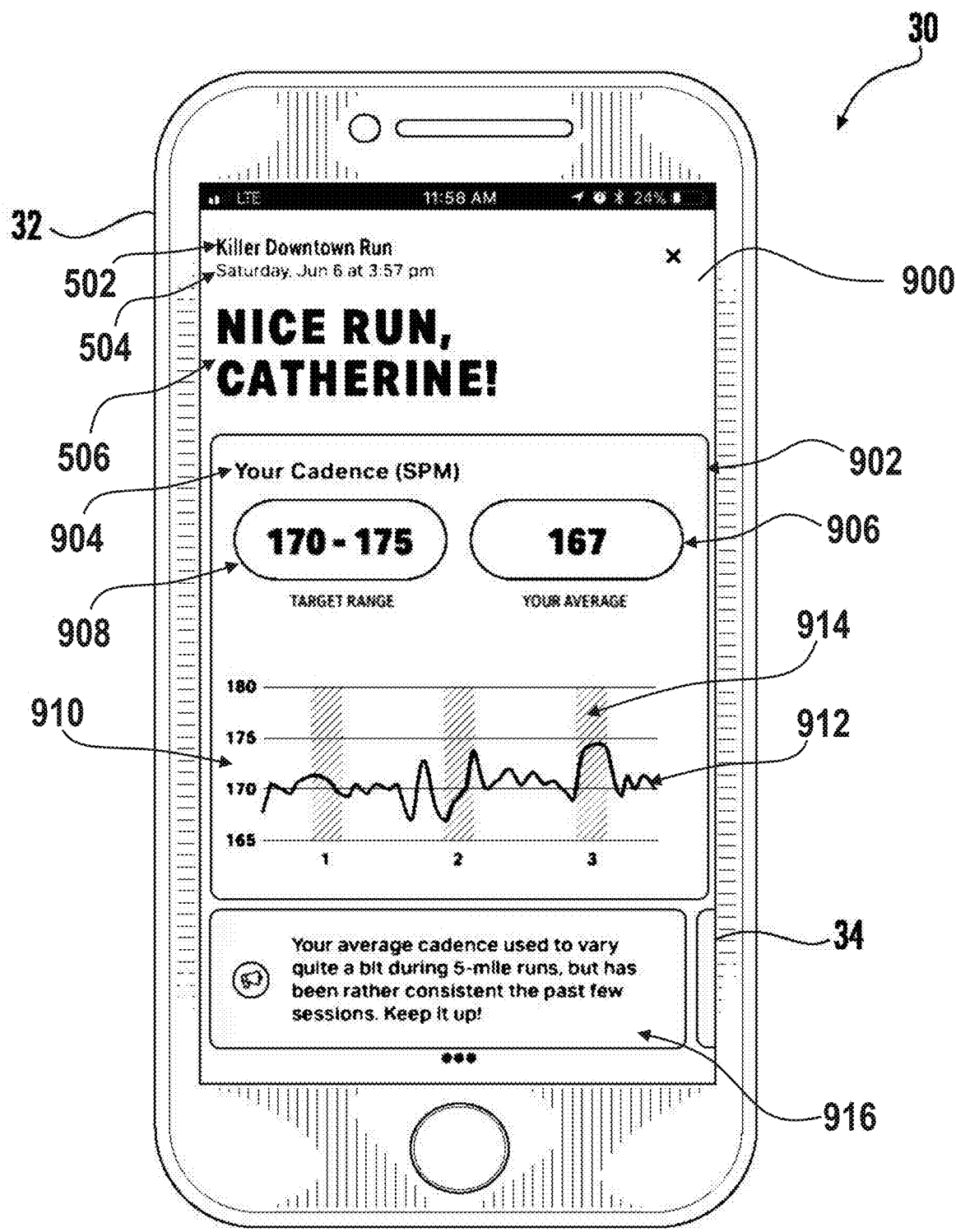
FIG. 19 is a plan view showing an exemplary gait coaching screen that is displayed after a run that included form intervals.

FIG. 19 shows an exemplary gait coaching screen 900 displayed on the display screen 34 of the electronic display device 30, which is displayed after a run that included form intervals. Much like the gait coaching screens 500a and 500d, the gait coaching screen 900 includes the title 502 (e.g. "Killer Downtown Run"), which may be generated automatically or chosen by the user, the time/date 504 (e.g., "Saturday, June 6 at 3:57 pm") that indicates the time and date at which the run was performed, and the encouragement message 506 (e.g., "NICE RUN, CATHERINE!"). However, the gait coaching screen 900 includes a gait metric comparison 902 which reflects that form intervals were performed during the run.

The gait metric comparison 902 includes a title 904 (e.g., "Your Cadence (SPM)"), a gait metric 906 having a value and label (e.g., a value "167" for "YOUR AVERAGE") and a gait metric target 908 having a value and label (e.g., a value "170-175" for the "TARGET RANGE"), which are similar to the features of previously discussed gait coaching screens. The gait metric comparison 902 includes a graph 910 which depicts a gait metric value 912 over time during the run and form intervals 914. In one embodiment, the processor 37 is configured to shade, color, or otherwise mark intervals of time in the graph 910 that correspond to the form intervals 914. Finally, the gait coaching screen 900 includes gait metric tips 916, which are similar to the gait metric tips discussed with respect to previously described gait coaching screens.

The herein described applications (e.g., the client-side activity tracking application and the network-side activity tracking application) improve the functioning of the electronic display device 30, the remote system server 40, and/or activity tracking devices 20a, 20b, respectively or in combination by enabling it/them to provide gait coaching which is individualized to a physiological characteristics of a particular user and to the pace of a particular run. As discussed above, the method 200 improves upon the functioning of the processor 47 of the system server 40 and/or the processor 37 of the electronic display device 30 by providing a gait metric model that advantageously incorporates running data from a broad diverse population of users, but also specifically considers running data from expert runners. Particularly, the 'shape' of the gait metric model is determined based on running data from a broad diverse population of users, thereby providing a robust estimation of how pace and physiological characteristics such height, age, weight, and sex influence the value for the at least one gait metric. At the same time, the offset and/or Y-axis intercept of the gait metric model is determined based on expert running data from a more limited set of expert users, thereby providing a better indication of what an optimal and/or efficient value for the at least one gait metric. Devices that are able to use the gait metric model developed in this way can operate more efficiently to provide useful and effective gait coaching to users.

Particularly, as discussed above, the method 300 improves upon the functioning of the processor 37 of the electronic display device 30 and/or the processor 27a, 27b of the activity monitoring device(s) 20a, 20b by advantageously providing the runner with an evaluation of his or her running gait in comparison with an optimal running gait that is determined based on the particular physiological characteristics of the individual and based on the particular pace of the individual run. In this way, the user can be confident in how to modify his or her running gait during his or her next run. Similarly, the method 600 improves upon the functioning of the processor 37 of the electronic display device 30 and/or the processor 27a, 27b of the activity monitoring device(s) 20a, 20b by advantageously providing the runner with a real-time evaluation of his or her running gait in comparison with an optimal running gait that is determined based on the particular physiological characteristics of the individual and based on the real-time pace during the run. In this way, the user can more easily learn to run with an ideal and efficient gait.

In another embodiment, a permanent copy of the programming instructions for individual ones of the aforementioned applications (e.g., the client-side activity tracking application and the network-side activity tracking application) may be placed into permanent storage devices (such as e.g., memory 28a, 28b, memory 38, and/or memory 48) during manufacture thereof, or in the field, through e.g., a distribution medium (not shown), such as a compact disc (CD), or through the transmitter/receiver 29a, 29b and/or the transmitter/receiver 39 (from the system server 40). That is, one or more distribution media having an implementation of the agent program may be employed to distribute the agent and program various computing devices.

The foregoing detailed description of one or more exemplary embodiments of the activity tracking application has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A method of displaying run data, comprising:
receiving first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length;
determining regression coefficients for at least one gait metric model by performing a regression of the first historical run data, the at least one gait metric model being configured to output the gait metric given inputs of pace and the at least one physiological characteristic;
receiving second historical run data regarding runs of a second plurality of users, the second historical run data including, for each run, the gait metric for the respective run, a pace during the respective run, and the at least one physiological characteristic of the respective user;
determining a regression constant for the at least one gait metric model by performing a regression of the second historical run data;
receiving first run data from an activity monitoring device carried by a first user during a first run of the first user;
determining the gait metric for the first run based on the first run data;
determining a pace during the first run based on the first run data;
determining a gait metric target for the first run based on the at least one gait metric model, the determined regression coefficients, the determined regression constant, the pace during the first run, and the at least one physiological characteristic of the first user, wherein the at least one gait metric model includes a pace term multiplied by a corresponding one of the regression coefficients and a pace squared term multiplied by a corresponding one of the regression coefficients such that the at least one gait metric model is expressed as:

the gait metric=$A^*$(height)+$B^*$(weight)+$C^*$(sex)+$D^*$(age)+$E^*$(pace)+$F^*$(pace)$^2$+$G$, where A, B, C, D, E, and F are the regression coefficients and G is the regression constant; and displaying a comparison of the gait metric with the gait metric target to the first user on a personal electronic device associated with the first user.

2. The method of claim 1, the displaying the comparison further comprising:
displaying the comparison after a completion of the first run by the first user and prior to a beginning of a second run by the first user, the second run being subsequent in time compared to the first run.

3. The method of claim 2, further comprising:
displaying instructions to the first user regarding the gait metric based on the comparison on the personal electronic device associated with the first user after the completion of the first run by the first user and prior to the beginning of the second run by the first user.

4. The method of claim 3, the displaying the instructions further comprising:
displaying the instructions to the first user in response to the first user beginning the second run.

5. The method of claim 2, the displaying the comparison further comprising:
if the first user has recorded run data for less than a predetermined number of runs, then displaying an average of the gait metric in comparison with an average of the gait metric target over the first run; and
if the first user has recorded run data for at least the predetermined number of runs, then displaying a graph depicting the gait metric in comparison with the gait metric target over time during the first run.

6. The method of claim 1, the displaying the comparison further comprising:
displaying the comparison of the gait metric with the gait metric target in relation to a previous comparison of a previous gait metric and a previous gait metric target corresponding to a previous run that was performed prior to the first run.

7. A fitness tracking system:
a database configured to store:
first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length; and
second historical run data regarding runs of a second plurality of users, the second historical run data including, for each run, the gait metric for the respective run, a pace during the respective run, and the at least one physiological characteristic of the respective user; and
a data processor in communication with the database, the data processor being configured to:
receive the first historical run data and the second historical run data from the database;
determine regression coefficients for at least one gait metric model by performing a regression of the first historical run data, the at least one gait metric model being configured to output the gait metric given inputs of pace and the at least one physiological characteristic;
determine a regression constant for the at least one gait metric model by performing a regression of the second historical run data, wherein the at least one gait metric model is expressed as:

the gait metric=$A^*$(height)+$B^*$(weight)+$C^*$(sex)+$D^*$(age)+$E^*$(pace)+$F^*$(pace)$^2$+$G$, where A, B, C, D, E, and F are the regression coefficients and G is the regression constant; and
transmit the regression coefficients and the regression constant for the at least one gait metric model to at least one personal electronic device of at least one user.

8. The fitness tracking system of claim 7, wherein the first historical run data was generated at least in part by a plurality of activity sensors carried by users in the first plurality of users during the runs of the first plurality of users, at least some sensors in the plurality of activity sensors being integrated with footwear worn by users in the first plurality of users during the runs of the first plurality of users.

9. The fitness tracking system of claim 7, wherein the second plurality of users is a subset of the first plurality of user that have recorded run data for at least a predetermined threshold number of runs.

10. A method of displaying run data, comprising:
receiving first historical run data regarding runs of a first plurality of users, the first historical run data including, for each run, a gait metric for the respective run, a pace during the respective run, and at least one physiological characteristic of the respective user, the gait metric being at least one of (i) a stride cadence and (ii) a stride length;
determining regression coefficients for at least one gait metric model by performing a regression of the first historical run data, the at least one gait metric model being configured to output the gait metric given inputs of pace and the at least one physiological characteristic;
receiving second historical run data regarding runs of a second plurality of users, the second historical run data including, for each run, the gait metric for the respective run, a pace during the respective run, and the at least one physiological characteristic of the respective user;
determining a regression constant for the at least one gait metric model by performing a regression of the second historical run data;
receiving first real-time run data from an activity monitoring device carried by a first user during a first run of the first user;
determining a real-time value of the gait metric during the first run based on the first real-time run data;
determining a real-time pace during the first run based on the first real-time run data;
determining a real-time gait metric target during the first run based on the at least one gait metric model, the determined regression coefficients, the determined regression constant, the real-time pace during the first run, and the at least one physiological characteristic of the first user; and
providing perceptible feedback to the first user during the first run depending on a comparison of the real-time value of the gait metric with the real-time gait metric target to the first user using a personal electronic device associated with the first user;
wherein the at least one gait metric model is expressed as:

the gait metric=$A^*$(height)+$B^*$(weight)+$C^*$(sex)+$D^*$(age)+$E^*$(pace)+$F^*$(pace)$^2$+$G$, where A, B, C, D, E, and F are the regression coefficients and G is the regression constant.

11. The method of claim 10, the providing the perceptible feedback further comprising:

displaying the perceptible feedback to the first user on a display device associated with the first user.

12. The method of claim 10, the providing the perceptible feedback further comprising:
audibly providing the perceptible feedback to the first user using an audio device associated with the first user.

13. The method of claim 10, the providing the perceptible feedback further comprising:
providing a feedback message instructing the first user to adjust the gait metric in response to the real-time value of the gait metric being outside a predetermined range of the real-time gait metric target.

14. The method of claim 10, the providing the perceptible feedback further comprising:
providing a feedback message instructing the first user to maintain the real-time gait metric target at one of (i) a defined time during the first run and (ii) a defined distance traveled during the first run.

15. The method of claim 10, further comprising:
providing an instruction to the first user to maintain the real-time gait metric target during a first interval of time during the first run; and
monitoring whether the real-time value of the gait metric is within a predetermined range of the real-time gait metric target during the first interval of time.

16. The method of claim 15, the providing the perceptible feedback further comprising:
providing a feedback message indicating whether the real-time value of the gait metric is within the predetermined range during the first interval of time.

17. The method of claim 15, the providing the perceptible feedback further comprising:
displaying a comparison of the real-time value of the gait metric with the real-time gait metric target during the first interval of time on a display device associated with the first user.

* * * * *